United States Patent
Ling et al.

(10) Patent No.: US 11,717,580 B2
(45) Date of Patent: Aug. 8, 2023

(54) CYCLODEXTRIN-LINKED POLYVALENT LIGANDS FOR COMPLEXATION OF METAL IONS

(71) Applicants: UTI LIMITED PARTNERSHIP, Calgary (CA); CENTRE NATIONAL DE LA RECHERCHE SCIENTIFIQUE, Paris (FR)

(72) Inventors: Chang-Chun Ling, Calgary (CA); Pier-Luc Champagne, Calgary (CA); Ping Zhang, Calgary (CA); Géraldine Gouhier, Mount Saint Aignan (FR)

(*) Notice: Subject to any disclaimer, the term of this patent is extended or adjusted under 35 U.S.C. 154(b) by 150 days.

(21) Appl. No.: 17/053,146

(22) PCT Filed: May 7, 2019

(86) PCT No.: PCT/CA2019/050603
§ 371 (c)(1),
(2) Date: Nov. 5, 2020

(87) PCT Pub. No.: WO2019/213756
PCT Pub. Date: Nov. 14, 2019

(65) Prior Publication Data
US 2021/0236661 A1 Aug. 5, 2021

Related U.S. Application Data

(60) Provisional application No. 62/667,954, filed on May 7, 2018.

(51) Int. Cl.
| | |
|---|---|
| *A61K 49/12* | (2006.01) |
| *A61K 49/08* | (2006.01) |
| *C02F 101/20* | (2006.01) |
| *C02F 1/68* | (2023.01) |
| *C02F 101/00* | (2006.01) |

(52) U.S. Cl.
CPC .......... *A61K 49/124* (2013.01); *A61K 49/085* (2013.01); *A61K 49/122* (2013.01); *C02F 1/683* (2013.01); *C02F 2101/006* (2013.01); *C02F 2101/20* (2013.01)

(58) Field of Classification Search
None
See application file for complete search history.

(56) References Cited

U.S. PATENT DOCUMENTS

| | | | |
|---|---|---|---|
| 7,385,041 | B2 | 6/2008 | Chang et al. |
| 2009/0155181 | A1 | 6/2009 | Rowe |
| 2011/0243857 | A1 | 10/2011 | Gouhier et al. |
| 2015/0210781 | A1 | 7/2015 | Bouckaert et al. |

OTHER PUBLICATIONS

Abboud et al., "Basicity of N-H- and N-Methyl-1,2,3-Triazoles in the Gas Phase, in Solution, and in the Solid State—An Experimental and Theoretical Study," *Eur. J. Org. Chem.*, pp. 3013-3024, 2001.

Aime et al., "Contrast Agents for Magnetic Resonance Imaging: A Novel Route to Enhanced Relaxivities Based on the Interaction of a $Gd^{III}$ Chelate with Poly-β-Cyclodextrins," *Chem. Eur. J.*, vol. 5:1253-1260, 1999.

Aime et al., "High-Relaxivity Contrast Agents for Magnetic Resonance Imaging Based on Multisite Interactions between a β-Cyclodextrin Oligomer and Suitably Functionalized $Gd^{III}$ Chelates," *Chem. Eur. J.*, vol. 7:5261-5269, 2001.

Aime et al., "β-Cyclodextrin Adducts of Gd(III) Chelates: Useful Models for Investigating the Structural and Dynamic Determinants of the Relaxivity of Gadolinium-Based Systems," *Magn. Reson. Chem.*, vol. 41:800-805, 2003.

Aime et al., New Paramagnetic Supramolecular Adducts for MRI Applications Based on Non-Covalent Interactions between Gd(III)-Complexes and β- or γ-Cyclodextrin Units Anchored to Chitosan,: *J. Inorg. Biochem.*, vol. 100:931-938, 2006.

Aime et al., "New Cyclodextrin Dimers and Trimers Capable of Forming Supramolecular Adducts with Shape-Specific Ligands," *Org. Biomol. Chem.*, vol. 7:370-379, 2009.

Almant et al., "Clustering of *Escherichia coli* Type-1 Fimbrial Adhesions by Using Multimeric Heptyl $\alpha$-$_D$-Mannoside Probes with a Carbohydrate Core," *Chem. Eur. J.*, vol. 17:10029-10038, 2011.

Barge et al., "New CD Derivatives as Self-Assembling Contrast Agents for Magnetic Resonance Imaging (MRI)," *J. Incl. Phenom. Macrocycl. Chem.*, vol. 57:489-495, 2007.

Barge et al., "Design and Synthesis of a $\gamma^{1\beta 8}$-Cyclodextrin Oligomer: A New Platform with Potential Application as a Dendrimeric Multicarrier," *Chem. Eur. J.*, vol. 19:12086-12092, 2013.

Battistini et al., "High-Relaxivity Magnetic Resonance Imaging (MRI) Contrast Agent Based on Supermolecular Assembly between a Gadolinium Chelate, a Modified Dextran, and Poly-β-Cyclodextrin," *Chem. Eur. J.*, vol. 14:4551-4561, 2008.

Biscotti et al., "MRI Probes Based on C6-Peracetate P-Cyclodextrins: Synthesis, Gadolinium Complexation and in vivo Relaxivity Studies," *Polyhedron*, vol. 148:32-43, 2018.

Bonnet et al., "A Rigorous Framework to Interpret Water Relaxivity. The Case Study of a Gd(III) Complex with an α-Cyclodextrin Derivative," *J. Am. Chem. Soc.*, vol. 130:10401-10413, 2008.

Bouckaert et al., "Heptyl $\alpha$-$_D$-Mannosides Grafted on a β-Cyclodextrin Core to Interfere with *Escherichia coli* Adhesion: An In Vivo Multivalent Effect," *Chem. Eur. J.*, vol. 19:7847-7855, 2013.

(Continued)

*Primary Examiner* — Jennifer Lamberski
(74) *Attorney, Agent, or Firm* — Klarquist Sparkman, LLP

(57) ABSTRACT

Compounds are described which include polyvalent ligands linked to a cyclodextrin scaffold which exhibit strong binding affinities for lanthanides and favorable characteristics with respect to altering the relaxation time of coordinated water molecules. The compounds are useful as contrast agents in applications such as magnetic resonance imaging. The polyvalent ligands are also useful in applications requiring chelation of metal ions in other applications such as water treatment, sequestration of metal ions and treatment of diseases or conditions caused by exposure to toxic or radioactive metal ions.

20 Claims, 13 Drawing Sheets

(56) References Cited

OTHER PUBLICATIONS

Bryson et al., "A β-Cyclodextrin "Click Cluster" Decorated with Seven Paramagnetic Chelates Containing Two Water Exchange Sites," *Bioconjug. Chem.*, vol. 19:1505-1509, 2008.
Burgess et al., "Hydroxypyranones, Hydroxypyridinones, and Their Complexes," *Adv. Inorg. Chem.*, vol. 60:167-243, 2008.
Cacheris et al., "The Relationship between Thermodynamics and the Toxicity of Gadolinium Complexes," *Mag. Res. Imag.*, vol. 8:467-481, 1990.
Caravan et al., "Gadolinium(III) Chelates as MRI Contrast Agents: Structure, Dynamics, and Applications," *Chem. Rev.*, vol. 99:2293-2352, 1999.
Champagne et al., "Synthesis and Unprecedented Complexation Properties of β-Cyclodextrin-Based Ligand for Lanthanide Ions," *Inorg. Chem.*, vol. 57:8964-8977, 2018.
Datta et al., "Gd-Hydroxypyridinone (HOPO)-Based High-Relaxivity Magnetic Resonance Imaging (MRI) Contrast Agents," *Acc. Chem. Res.*, vol. 42:938-947, 2009.
Fatin-Rouge et al., "Thermodynamic and Structural Study of Inclusion Complexes between Trivalent Lanthanide Ions and Native Cyclodextrins," *Inorg. Chimica Acta*, vol. 293:53-60, 1999.
Fraum et al., "Gadolinium-Based Contrast Agents: A Comprehensive Risk Assessment," *J. Magn. Reson. Imaging*, vol. 46:338-353, 2017.
Fredy et al., "Cyclodextrin Polyrotaxanes as a Highly Modular Platform for the Development of Imaging Agents," *Chem. Eur. J.*, vol. 20:10915-10920, 2014.
Fredy et al., "Mechanostereoselective One-Pot Synthesis of Functionalized Head-to-Head Cyclodextrin [3]Rotaxanes and Their Application as Magnetic Resonance Imaging Contrast Agents," *Org. Lett.*, vol. 19:1136-1139, 2017.
Gianolio et al., "Poly-β-Cyclodextrin Based Platform for pH Mapping via a Ratiometric $^{19}F/^{1}H$ MRI Method," *Chem. Commun.*, pp. 6044-6046, 2009.
Harborg et al., "Assay of the Active Ingredient of an MRI Contrast Agent using Mid and Near Infrared Spectroscopy and Multivariate Calibration," *J. Mol. Struct.*, vol. 348:139-142, 1995.
Hermann et al., "Gadolinium(III) Complexes as MRI Contrast Agents: Ligand Design and Properties of the Complexes," *Dalton Trans.*, No. 23:3027-3047, 2008.
Idée et al., "Possible Involvement of Gadolinium Chelates in the Pathophysiology of Nephrogenic Systemic Fibrosis: A Critical Review," *Toxicol.*, vol. 248:77-88, 2008.
Idriss et al., "Effect of the Second Coordination Sphere on New Contrast Agents Based on Cyclodextrin Scaffolds for MRI Signals," *RSC Adv.*, vol. 3:4531-4534, 2013.
International Search Report dated Jul. 4, 2019 for International Application No. PCT/CA2019/050603, 5 pages.
International Preliminary Report on Patentability and Written Opinion dated Nov. 10, 2020 for International Application No. PCT/CA2019/050603, 7 pages.
Kotková et al., "Cyclodextrin-Based Bimodal Fluorescence/MRI Contrast Agents: An Efficient Approach to Cellular Imaging," *Chem. Eur. J.*, vol. 16:10094-10102, 2010.
Kotkova et al., "Gadolinium Complexes of Monophosphinic Acid DOTA Derivatives Conjugated to Cyclodextrin Scaffolds: Efficient MRI Contrast Agents for Higher Magnetic Fields," *Dalton Trans.*, vol. 41:13509-13519, 2012.
Long et al., "Metabolomic Profiles Delineate Potential Roles for Gadolinium Chloride in the Proliferation or Inhibition of Hela Cells," *Biometals*, vol. 24:663-677, 2011.
Liu et al., "Multifunctional pH-Disintegrable Micellar Nanoparticles of Asymmetrically Functionalized β-Cyclodextrin-Based Star Copolymer Covalently Conjugated with Doxorubicin and DOTA-Gd Moieties," *Biomaterials*, vol. 33:2521-2531, 2012.
Maffeo et al., "Novel Polycarboxylated EDTA-Type Cyclodextrins as Ligands for Lanthanide Binding: Study of their Luminescence, Relaxivity Properties of Gd(III) Complexes, and PM3 Theoretical Calculations," *Org. Biomol. Chem.*, vol. 8:1910-1921, 2010.
Martinelli et al., "Cleavable β-Cyclodextrin Nanocapsules Incorporating $Gd^{III}$-Chelates as Bioresponsive MRI Probes," *Chem. Commun.*, vol. 47:3144-3146, 2011.
Martinelli et al., "Dendrimeric β-Cyclodextrin/$Gd^{III}$ Chelate Supramolecular Host-Guest Adducts as High-Relaxivity MRI Probes," *Chem. Eur. J.*, vol. 20:10944-10952, 2014.
Rashid et al. "Cyclen-based $Gd^{3+}$ Complexes as MRI Contrast Agents: Relaxivity Enhancement and Ligand Design," *Bioorg. Med. Chem.*, vol. 24:5663-5684, 2016.
Rudovsky et al., "Relaxometric and Solution NMR Structural Studies on Ditopic Lanthanide(III) Complexes of a Phosphinate Analogue of DOTA with a Fast Rate of Water Exchange," *Dalton Trans.*, pp. 2323-2333, 2006.
Schlaudecker et al., "Gadolinium-Associated Nephrogenic Systemic Fibrosis," *Am. Fam. Physician*, vol. 80:711-714, 2009.
Skinner et al., "Conjugates of Cyclodextrins with Charged and Neutral Macrocyclic Europium, Terbium and Gadolinium Complexes: Sensitised Luminescence and Relaxometric Investigations and an Example of Supramolecular Relaxivity Enhancement," *J. Chem. Soc. Perkin Trans.*, vol. 2:1329-1338, 2000.
Supkowski et al., "On the Determination of the Number of Water Molecules, q, Coordinated to Europium(III) Ions in Solution from Luminescence Decay Lifetimes," *Inorg. Chimica Acta*, vol. 340:44-48, 2002.
Thomsen, "Generic Gadolinium-based Contrast Agents: The Future? ", *Acta Radiol.*, vol. 58:1285-1287, 2017.
Tweedie et al., "Biodistribution of Radiolabeled, Formulated Gadopentetate, Gadoteridol, Gadoterate, and Gadodiamide in Mice and Rats," *Invest. Radiol.*, vol. 30:372-380, 1995.
Zgani et al., "Positive Variation of the MRI Signal via Intramolecular Inclusion Complexation of a C-2 Functionalized β-Cyclodextrin," *Org. Biomol. Chem.*, vol. 15:564-569, 2017.
Zhou et al., "Gd3+-1,4,7, 10-Tetraazacyclodecane-1,4,7-Triacetic-2-hydroxypropyl-β-cyclodextrin/Pluronic Polyrotaxane as a Long Circulating High Relaxivity MRI Contrast Agent," *ACS Appl. Mater. Interfaces*, vol. 7:22272-22276, 2015.

Reagents and conditions:
a) MeOH/AcCl, 60 °C, overnight (~100%);
b) Propargyl bromide/DIPEA/CH$_2$Cl$_2$, 40 °C, overnight (65%);
c) CuI/DIPEA/acetone, 55 °C, overnight (77%);
d) NaOMe/MeOH/CH$_2$Cl$_2$, then NaOH/H$_2$O-MeOH, 70 °C, overnight (84%).

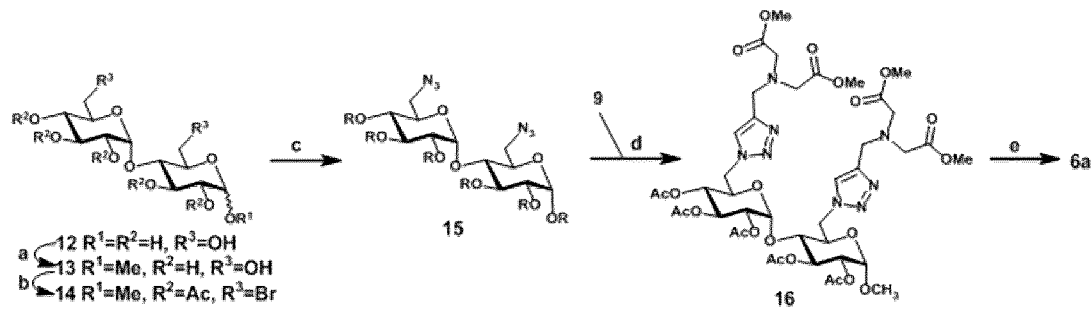

Reagents and conditions:
a) MeOH/p-TsOH, reflux, overnight (30%);
b) PPh₃/NBS/DMF, 60 °C, 4 h,
   then Ac₂O/Pyridine, 50 °C, overnight;
c) NaN₃/DMF, 90 °C, 18 h (48%, 3 steps);
d) CuI/DIPEA/acetone, 55 °C, overnight (71%);
e) NaOMe/MeOH/CH2Cl2, then
   NaOH/H2O-MeOH, 70 °C, overnight (92%).

Fig. 3A

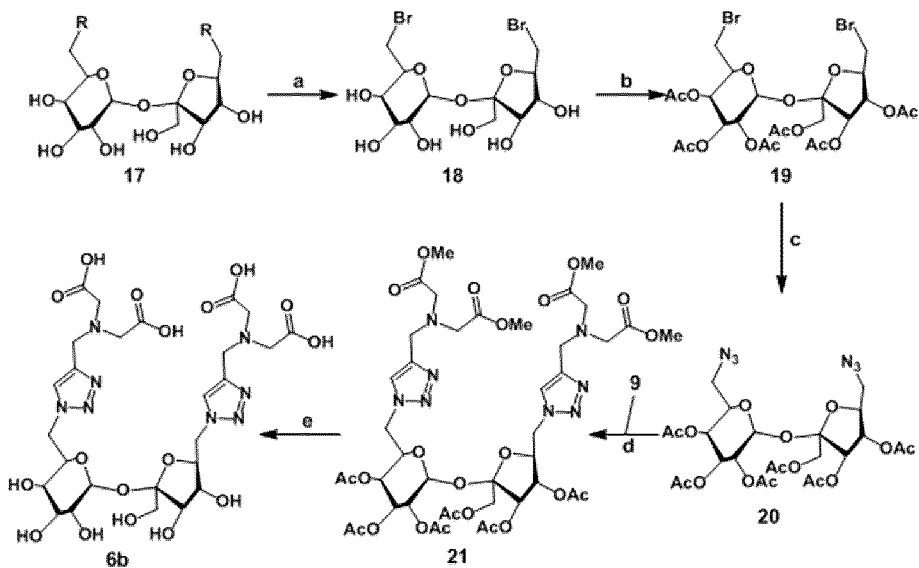

Reagents and conditions:
a) PPh₃/CBr₄/pyridine, 80 °C, 4 h;
b) Ac₂O/Pyridine, 50 °C, 5 h;
c) NaN₃/DMF, 80 °C, 18 h;
d) CuI/DIPEA/acetone, 55 °C, overnight;
e) NaOMe/MeOH/CH₂Cl₂, then
   NaOH/H₂O-MeOH, 70 °C, overnight.

Fig. 3B

M³⁺: Y³⁺, Gd³⁺ etc

CYCLODEXTRIN-LINKED POLYVALENT LIGANDS FOR COMPLEXATION OF METAL IONS

CROSS REFERENCE TO RELATED APPLICATIONS

This is the U.S. National Stage of International Application No. PCT/CA2019/050603, filed May 7, 2019, which was published in English under PCT Article 21(2), which claims the benefit of U.S. Provisional Application No. 62/667,954, filed May 7, 2018, which is herein incorporated by reference in its entirety.

TECHNICAL FIELD

The invention relates to compounds comprising polyvalent ligands linked to a cyclodextrin scaffold. The compounds exhibit strong binding affinities for lanthanides and favorable characteristics with respect to altering the relaxation time of coordinated water molecules. The compounds are useful as contrast agents in applications such as magnetic resonance imaging, as well as heavy metal detoxification and sequestration.

BACKGROUND

The use of contrast agents has transformed magnetic resonance imaging (MRI) to become one of the most powerful and versatile diagnostic tools in modern clinical medicine.[1-3] Contrast agents are commonly based on complexes of gadolinium (III), a paramagnetic lanthanide that possesses optimal coordination chemistry. For example, the highly toxic metal provides a 9-coordination sphere available for potential dynamic water coordination, resulting in catalytic alteration of relaxivities of proton nuclei of water. This creates significant contrasts to relaxivities of non-coordinated water molecules located in other tissues, leading to improved resolution of acquired images. Currently, approximately 35% of MRI scans require the use of a contrast agent. To circumvent the toxicity of Gd(III), polyaminocarboxylate-based ligands[4] such as the linear diethylenetriaminepentaacetic acid (DTPA) and cyclic 1,4,7,10-tetraazacyclododecane-1,4,7,10-tetraacetic acid (DOTA) as well as their derivatives are used in clinics to form highly stable complexes (1 and 2, FIG. 1) with Gd(III); the determined affinities are remarkably high with the cyclic ligand (Log $K_{Gd}$-DOTA~25.2) which is slightly higher than the linear analog (Log $K_{Gd}$-DTPA~22.5).

Due to the adverse effects[5] associated with gadolinium complexes, such as gadolinium-associated nephrogenic systemic fibrosis,[6,7] the DTPA-based contrast agents are no longer authorized for administration in some countries, leaving only a few DOTA-based contrast agents available for clinical use.[8] This creates urgent needs for the development of new contrast agents.

Cyclodextrins represent a class of promising scaffolds for the design of a new generation of MRI probes due to their biocompatibility, large molecular weights and multivalency as well as their hydrophobic cavities. During last decade, there has been considerable interest to develop cyclodextrin-based MRI probes.[9-27] However, most these reports were based on a common strategy consisting of either covalently grafting one or multiple units of known chelating motifs such as DTPA or DOTA onto a monomeric[9-13] or oligo/polymeric cyclodextrin[14-21] backbone or forming an inclusion complex.[11,16,17,21-27] The new derivatives generally possess improved relaxivities due to their reduced tumbling rate, which is influenced by the marked increase in molecular weights in the newly generated systems, compared to the commercial contrast agents with low molecular weights. Logically, all Gd(III) complexes generated using this strategy should be as stable as the commercially available contrast agents (see compounds 1 and 2 in FIG. 1).

On the other hand, another strategy to develop cyclodextrin-based MRI probes consists of taking advantage of the native macrocyclic geometry to create an innovative coordination sphere for Gd(III). Such an approach has the potential to generate new MRI probes with improved properties and reduced toxicity compared to DTPA and DOTA. However, this approach has only reached limited success, as there have been very few attempts reported in the literature to date and no cyclodextrin derivatives with binding affinity to Gd(III) comparable to DTPA or DOTA have been reported.[28-31] The reported literature examples can be classified into two families based on functionalizations. The first was based on per-6-amino-α/β/γ-cyclodextrins by carrying out a per-N,N-dialkylation with acetates to afford EDTA-type ligands such as the β-cyclodextrin analog 3 (FIG. 1).[28] Based on molecular modeling, it was proposed that every two units of iminodiacetates attached to the C6 positions of adjacent glucopyranosyl units in cyclodextrins were used to complex one metal ion, generating a coordination sphere of six valencies for each Gd(III) center (two amino groups and four acetates). Unfortunately, the binding affinities of these Gd-complexes were not reported. The inventors of the present application estimate that the affinities might likely be much lower than those of Gd-DOTA or Gd-DTPA complexes, due to the lower number of coordination per Gd(III) center, as well as potential tension introduced by the cyclodextrin scaffold, owing to the proximity of the metal coordination center to the primary rim of cyclodextrins, preventing each chelating arm from adopting optimal geometry for coordination. The second family consists of per-O-alkylations of cyclodextrin derivatives with acetates. Starting from 3,6-anhydro-α-cyclodextrin,[29] An O2-polyacetate was generated and reported to bind to one Gd(III) metal with a stability constant Log $K_{Gd}$ of 7.5 and with low toxicity as well as no nephrotoxicity or hemolysis on a rat model.

The inventors of the present application have also developed novel MRI probes such as the per-O6-acetate 4 from β-cyclodextrin via O6-alkylations.[39,31] These ligands were found to sequester one Gd(III) metal, and the formed complexes showed favorable alterations of water relaxivity, revealing their ability to form secondary hydration sphere. However, the coordination geometry of these per-O6-acetates with Gd(III) remains poorly understood and their binding affinities with Gd(III) are also similar to the O2-polyacetate.[32]

US Patent Publication No. 2011/0243857, incorporated herein by reference in its entirety, describes cyclodextrin-based compounds developed for use as MRI contrast agents. Subsequent unpublished investigations by one of the present inventors have indicated that these compounds have metal binding constants generally in the range of $10^8$.

There continues to be a need for development of contrast agents for MRI.

SUMMARY

One aspect of the invention is a compound of formula MAL), wherein,
M is a metal ion, Lisa ligand of the formula I: A-[W—X—Y—N(CH$_2$COO)$_2$]$_n$, and z is an integer of 1 to 4, wherein A is a cyclodextrin or a derivative thereof, a disaccharide or a derivative thereof, starch or other carbohydrate-based polymer;

W is a substituted or unsubstituted $C_1$-$C_5$ carbon chain;

X is a five or six membered ring having one or more heteroatoms;

Y is a substituted or unsubstituted $C_1$-$C_3$ carbon chain; and n is an integer of 2 to 8.

In certain embodiments, the heteroatoms are each independently nitrogen, oxygen or sulfur.

In certain embodiments, the five or six membered ring is an aromatic ring.

In certain embodiments, the five membered ring is imidazole or triazole.

In certain embodiments, the five membered ring is triazole.

In certain embodiments, W is a single unsubstituted aliphatic carbon.

In certain embodiments, Y is a single unsubstituted aliphatic carbon.

In certain embodiments, A is a cyclodextrin.

In certain embodiments, A is a cyclodextrin derivative including one or more glucopyranosyl units having one or both free hydroxyl groups replaced with an alkoxy group or an acyl group.

In certain embodiments, each of the glucopyranosyl units has both free hydroxyl groups replaced with an alkoxy group or an acyl group.

In certain embodiments, the alkoxy group is $C_1$-$C_4$ alkoxy.

In certain embodiments, the $C_1$-$C_4$ alkoxy group is $C_4H_9O$.

In certain embodiments, the cyclodextrin is an alpha-cyclodextrin, a beta-cyclodextrin, or a gamma-cyclodextrin.

In certain embodiments, the cyclodextrin is alpha-cyclodextrin and n is an integer of 2 to 6.

In certain embodiments, the cyclodextrin is beta-cyclodextrin and n is an integer of 2 to 7.

In certain embodiments, the cyclodextrin is gamma-cyclodextrin and n is an integer of 2 to 8.

In certain embodiments, the metal ion is a lanthanide ion, an actinide ion or a heavy metal ion.

In certain embodiments, the lanthanide ion is Gd(III), Yb(III) and Eu(III).

In certain embodiments, in formula I, W—X—Y—N(CH$_2$COO)$_2$ is

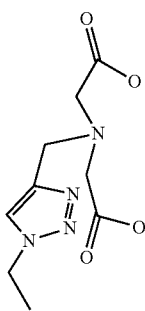 [SMILES: CCn1cc(CN(CC(=O)O)CC(=O)O)nn1]

In certain embodiments, the lanthanide ion has octahedral coordination provided by functional groups contained in two adjacent W—X—Y—N(CH$_2$COO)$_2$ moieties of the formula A-[W—X—Y—N(CH$_2$COO)$_2$]$_n$.

In certain embodiments, the octahedral coordination is:

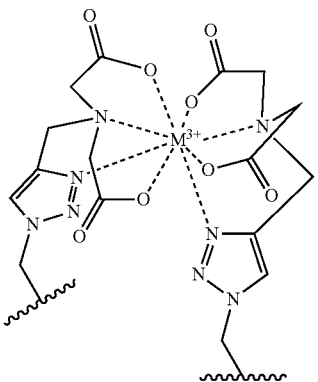

wherein the dashed lines indicate coordination bonds between the W—X—Y—N(CH$_2$COO)$_2$ moiety and the metal ion.

In certain embodiments, the W—X—Y—N(CH$_2$COO)$_2$ moiety is linked to the cyclodextrin at position C6 of one or more of the glucopyranosyl unit of the cyclodextrin.

In certain embodiments, the W—X—Y—N(CH$_2$COO)$_2$ moiety is linked to an amphiphilic cyclodextrin which has hydrophobic chains at either its primary face or secondary face.

In certain embodiments, A is a disaccharide and n is 2.

In certain embodiments, the disaccharide is maltose, sucrose, lactose, lactosamine, cellubiose or trehalose, or a derivative thereof.

In certain embodiments, the disaccharide is part of an oligosaccharide or a polysaccharide.

In certain embodiments, the metal ion is a lanthanide ion.

In certain embodiments, the metal ion is an actinide ion.

In certain embodiments, the metal ion is a heavy metal ion.

In certain embodiments, the heavy metal ion is toxic.

In certain embodiments, the heavy metal ion is radioactive.

In certain embodiments, the lanthanide ion is Gd(III), Yb(III), or Eu(III).

In certain embodiments, in formula A, W—X—Y—N(CH$_2$COO)$_2$ is

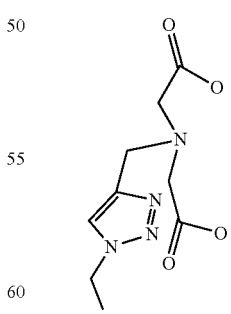

In certain embodiments, the metal ion has octahedral coordination geometry or any geometries less than octahedral coordination provided by functional groups contained in two adjacent W—X—Y—N(CH$_2$COO)$_2$ moieties of the formula A-[W—X—Y—N(CH$_2$COO)$_2$]$_n$.

In certain embodiments, the octahedral coordination geometry is:

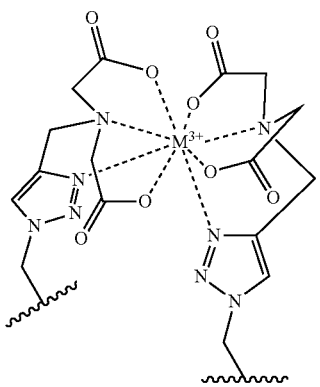

wherein the dashed lines indicate coordination bonds between the functional groups in the W—X—Y—N(CH$_2$COO)$_2$ moiety and the metal ion.

In certain embodiments, the W—X—Y—N(CH$_2$COO)$_2$ moiety is linked to the cyclodextrin at position C6 of each glucopyranosyl unit of the disaccharide.

Another aspect of the invention is a contrast agent comprising the compound described herein and a pharmaceutically acceptable carrier or diluent.

Another aspect of the invention is a method of acquiring an image, the method comprising: a) administering the contrast agent as described herein to a tissue, cell or patient; and b) acquiring a magnetic resonance image of the cell, tissue or patient.

Another aspect of the invention is a compound of formula I: A-[W—X—Y—N(CH$_2$COO)$_2$]$_n$,
wherein
A is cyclodextrin or a derivative thereof, a disaccharide or a derivative thereof, starch or other carbohydrate-based polymer;
W is a substituted or unsubstituted C$_1$-C$_5$ carbon chain;
X is a five or six membered ring having one or more heteroatoms;
Y is a substituted or unsubstituted C$_1$-C$_3$ carbon chain; and
n is an integer of 2 to 8.

Also provided is a use of the compound of formula I and derivatives thereof described herein for treatment of water by removal of metal ions from the water. The metal ions may be toxic or radioactive.

Also provided is a use of the compound of formula I and derivatives thereof described herein for treatment of water by removal of organic contaminants.

Also provided is a use of the compound of formula I and derivatives thereof described herein for sequestering and recovering metal ions.

Also provided is a use of the compound of formula I and derivatives thereof described herein for treatment of a disease or condition caused by the presence of heavy metal ions or radioactive metal ions.

BRIEF DESCRIPTION OF THE DRAWINGS

FIG. 3A shows a synthetic route for synthesis of maltoside ligand 6.

FIG. 3B shows a synthetic route for synthesis of sucrose ligand 22.

DETAILED DESCRIPTION

Rationale and Introduction

Figure 1:
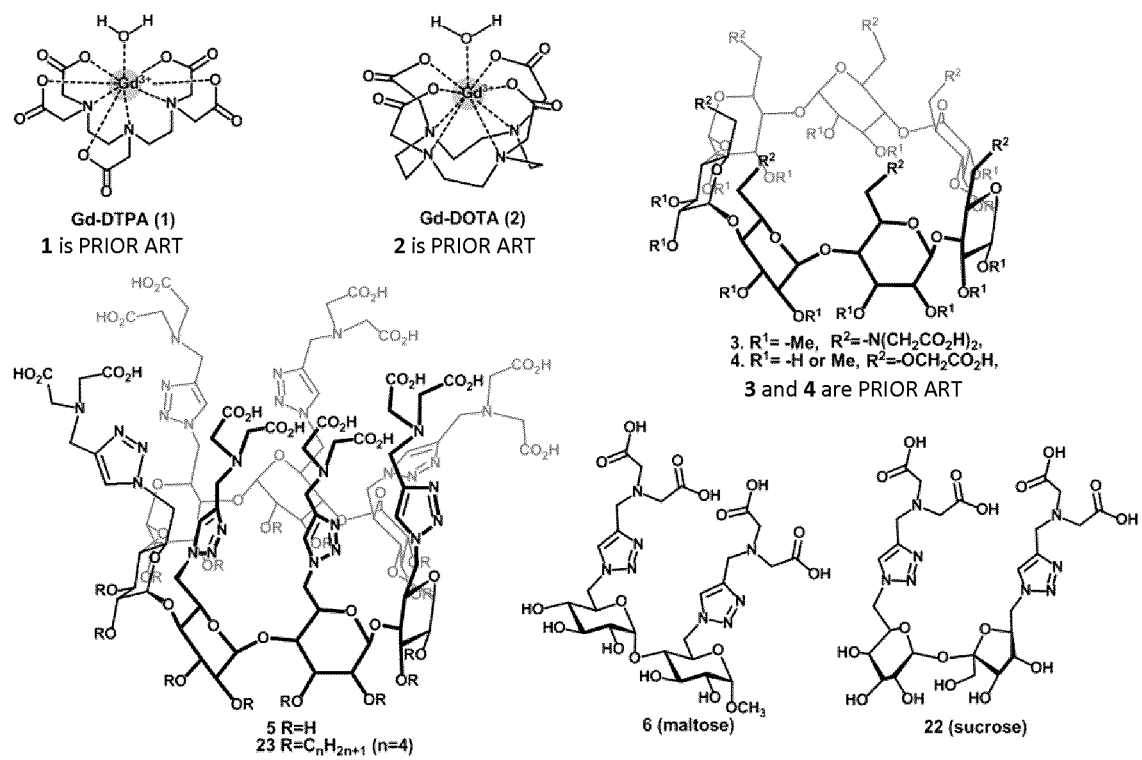
FIG. 1 shows structures of examples of known contrast agents Gd-DTPA(H$_2$O) (1); Gd-DOTA(H$_2$O) (2) and previously reported cyclodextrin-based ligands (3 and 4) for gadolinium(III) as well as new synthetic compounds 5, 6, 22 and 23.

Standard commercial MRI contrast agents based on DTPA and derivatives have problems with poor stability, release of free gadolinium (which is toxic), and allergic reactions. There is risk of nephrogenic systemic fibrosis which has led to reduced use of many MRI contrast agents in Europe. Other polymer-based contrast agents can be difficult for regulatory agencies to assess for safety due challenges relating to complete characterization of the polymers. These problems have motivated the present inventors to develop alternative compounds for use as contrast agents.

In accordance with one embodiment of the invention, there is provided a cyclodextrin-based MRI probe compound 5, linked to 7 copies of iminodiacetates that are connected to the C6 positions of β-cyclodextrin via a N-(1H-1,2,3-triazol-4-yl)methyl linker. The iminodiacetate moiety selected for provision of coordinating functional groups was originally selected because it is commercially available and inexpensive. In another embodiment, to assist in detailed binding studies, there is provided a second simplified compound 6 which is based on a methyl α-maltoside disaccharide that essentially represents a local copy of the coordination sphere found in compound 5. Both compounds provide one extra coordination valency to Gd(III) by the 1H-1,2,3-triazole unit, to potentially complete an 8-coordination sphere for lanthanide(III), with the aim of providing high affinity and high stability of the complex, while still leaving room for the coordination of one water molecule. Detailed binding studies with Gd(III) and are described herein to establish the stability constants of the formed complexes. The results indicate that this coordination chemistry may be used to generate high affinity ligands based on cyclodextrin scaffolds to sequester lanthanide metals. It is believed that the provision of a heteroatom in the ring of the linker moiety contributes significantly to the increase in affinity of the ligand for the metal ion and provides conformational flexibility to provide a favorable bond angle. While the binding of Gd(III) has been primarily investigated thus far, it is reasonably believed that other lanthanide ions such as Yb(III) and Eu(III), for example, will also be effectively bound by compounds described herein. Furthermore, it is reasonably predicted that the compounds described herein will be useful in binding other metal ions used in therapeutic applications, including radioactive metal ions for killing tumors, as well as in other applications such as detoxification of heavy metals, and sequestering heavy metals.

The target compound 5 is synthesized in a highly efficient manner from inexpensive and readily available iminodiacetic acid. The introduction of a propargyl group on the nitrogen of the iminodiacetate permits an efficient incorporation of the chelating groups into the cyclodextrin scaffold via the copper(I)-mediated 1,3-dipolar cycloaddition; this advantageously provides a 1,2,3-triazole unit that has the ideal linker length to allow the 1,2,3-triazole participating in the coordination of metals. Despite the structural complexity of compound 5, with the help of a simplified model compound 6 in which the cyclodextrin is replaced with maltoside (a disaccharide), the coordination chemistry of compounds 5 and 6 with lanthanides was investigated as described hereinbelow. It was confirmed that these compounds provide an octavalent coordination sphere for lanthanide metals with a remarkably high stability constant (comparable to the commercial DOTA-Gd(III)), while still being capable of sparing an additional site for dynamic water-coordination.

The new cyclodextrin ligand was found to form 1:1, 1:2, and 1:3 multinuclear complexes with lanthanides, thus it potentially has higher catalytic capacity during dynamic water-exchange. Lastly, the formed complexes also showed significantly improved abilities to alter relaxation time T1 of coordinated water than DOTA-Gd(III), which are even better than some of the known synthetic cyclodextrin-based probes including polymers. These characteristics, combined with the outstanding ability of compound 5 to prevent toxic Gd(III) from leaching back to solution (highest pGd), indicate that compound 5 has significant potential for development as an effective contrast agent for MRI as well as in other applications such as detoxification of heavy metals in the events of metal poisoning and water treatment, and sequestering heavy metals during mining.

Derivatized Cyclodextrins

Cyclodextrins are cyclic oligosaccharides consisting of at least six glucopyranose units. Although cyclodextrins with up to twelve glucopyranose units are known, only the first three homologs have been studied extensively, α-, β- and γ-having 6, 7 and 8 glucopyranose units, respectively. For example, the β-cyclodextrin molecule includes seven α-1, 4-linked glucopyranose units which form a cone-shaped molecule having a hydrophilic outer surface and a lipophilic cavity in the center. Cyclodextrins exist as conical shaped molecules with the primary hydroxyls situated at the small end of the cone and the secondary hydroxyls situated at the large opening to the cone.

Topographically, the cyclodextrins may be represented as a torus, the upper rim of which is lined with primary —CH$_2$OH groups, and the lower rim with secondary hydroxyl groups. Coaxially aligned with the torus is a channel-like cavity of about 5, 6 or 7.5 A.U. diameter for the α-, β- and γ-cyclodextrins, respectively. These cavities make the cyclodextrins capable of forming inclusion compounds with hydrophobic guest molecules of suitable diameters.

A reasonably large number of cyclodextrin derivatives have been prepared and described in the literature. In general, these chemically modified cyclodextrins are formed by reaction of the primary or secondary hydroxyl groups attached to carbons 2, 3 or 6 of the glucopyranose unit.

Synthesis of New Compounds

Figure 2:
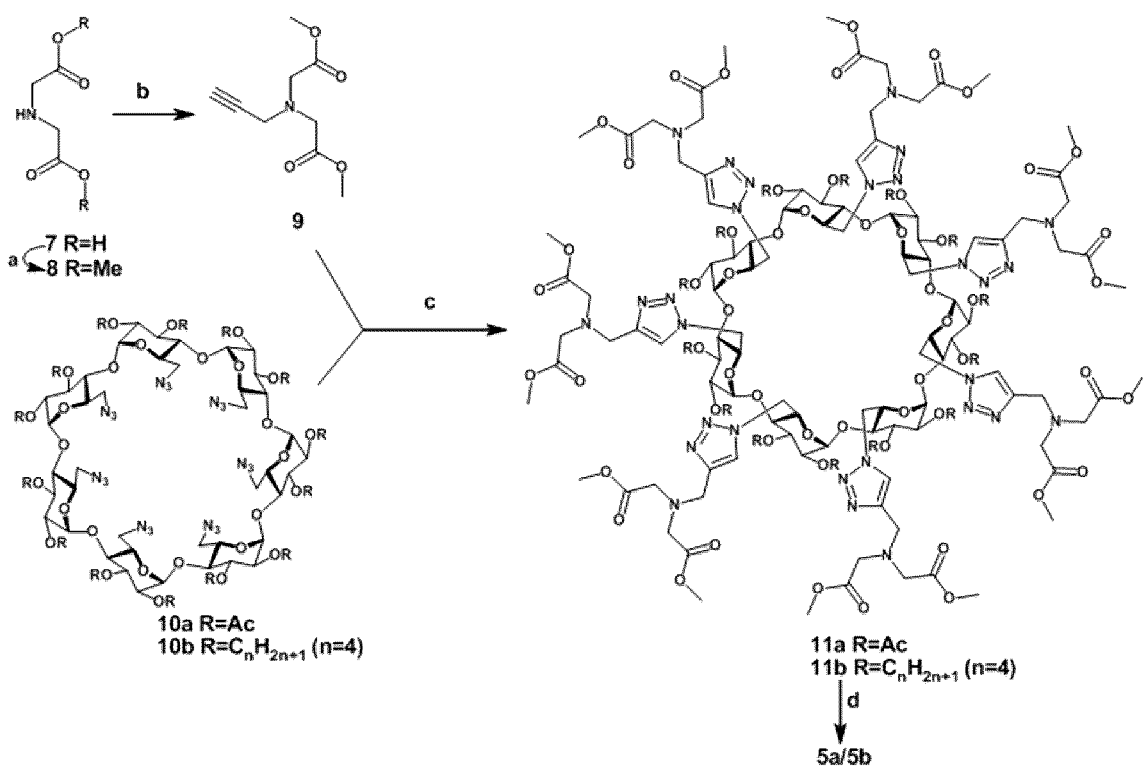
FIG. 2 shows a synthetic route for synthesis of compounds 5 and 23.

The desired compound 5 was effectively synthesized through a highly convergent route illustrated in FIG. 2. The commercially available iminodiacetic acid 7 was first O-methylated in anhydrous methanol at 60° C. overnight under strongly acidic conditions to provide the dimethyl ester 8, isolated in the hydrochloric acid salt form (~100% yield). The salt 8 was then N-alkylated with propargyl bromide in refluxing dichloromethane in the presence of excess diisopropylethylamine (DIPEA); this afforded the corresponding tertiary amine 9, isolated by column chromatography on silica gel in good yield (65%). The next step is the key conjugation between compound 9 and the fully acetylated per-6-azide 10a, synthesized according to literature from per-6-bromo-β-cyclodextrin in two steps.[33] The 1,3-dipolar cycloaddition was carried out using 1.5 equivalents of alkyne per azide in refluxing acetone using a catalytic amount of copper(I) iodide catalyst in presence of DIPEA; the reaction afforded the desired per-6-substituted conjugate 11a, isolated in 77% yield by column chromatography using a mixture of dichloromethane-methanol-triethylamine (98.5:0.5:1) as eluent.

The purity and identity of compound 11a was confirmed by $^1$H and $^{13}$C NMR spectroscopy and electrospray high-resolution mass spectrometry (ESI-HRMS). For example, a single 1,2,3-triazole peak was observed at 7.73 ppm combined with the anomeric protons of all glucopyranoses being observed at 5.53 as a doublet (J=3.3 Hz); this was further confirmed with the observed downfield shifts of all H-6a and H-6b protons from below 3.8 ppm to 4.93 and 4.83 ppm due to the significant deshielding effect of the newly formed 1,2,3-triazole rings. Furthermore, the ESI-HRMS spectrum in positive ion mode showed the expected doubly-charged ion at m/z 1646.5788, corresponding to the expected formula: $C_{133}H_{184}N_{28}O_{70}$ $(M+2H)^{2+}$ (calculated m/z: 1646.5844). The fully protected intermediate 11a was then deprotected by first carrying out a Zemplén transesterification to remove the 14 O-acetates on the secondary face, followed by a saponification reaction of all the remaining methyl esters using NaOH in a mixture of deionized water-methanol. The obtained crude product was finally purified by gel filtration on Sephadex G-15 to provide the desired compound 5 in high yield (84% yield).

An amphiphilic cyclodextrin ligand 23 was synthesized in a similar manner as compound 5 (FIG. 1), but using the per-6-azido-2,3-O-n-butyl-b-CD (11b) as the starting material. Compound 23 was isolated by gel filtration on Sephadex LH-20 using methanol as the eluent.

As shown in FIG. 3A, to quickly prepare compound 6, maltose 12 was first subjected to a Fisher glycosylation in refluxing anhydrous methanol in the presence of Amberlite IR-120 (H+). The crude mixture was then purified by column chromatography on silica gel to afford the desired methyl glycoside 13 as a 1:1 anomeric mixture (~30% yield). The two primary hydroxyl groups were then converted to the 6,6'-dibromide using N-bromosuccinimide (NBS)-triphenylphosphine as the reagent in anhydrous DMF at 70° C. followed by a per-O-acetylation with acetic anhydride in pyridine, and the crude compound 14 was then directly substituted by sodium azide in anhydrous DMF at 85° C. This afforded the corresponding 6,6'-diazide 15, which was also isolated by column chromatography on silica gel as an anomeric mixture (α/β-1:1, ~48% yield over 3 steps). With the help of HPLC on normal phase silica gel column, and using a gradient of 0→5% ethyl acetate-dichloromethane as eluent, the desired α-anomer 15 was partially isolated in pure form. The previously synthesized alkyne 9 was conjugated to the pure α-diazide 15 (71% yield) using similar conditions as above, this afforded the desired conjugate 16 in 71% yield. After sequential deprotection steps as above, the pure ligand 6 was obtained by gel filtration on Sephadex LH-20 (92% yield).

As shown in FIG. 3B, the synthetic strategy can be applied to the synthesis of sucrose-based ligand 22. The commercial sucrose 17 was first subjected to regioselective dibromination. The two primary hydroxyl groups at C-6 and C-6' positions were converted to the 6,6'-dibromide 18 using carbon tetrabromide-triphenylphosphine as the reagent in anhydrous pyridine at 80° C. This was followed by a per-O-acetylation with acetic anhydride in pyridine, and the obtained compound 19 was then directly substituted by sodium azide in anhydrous DMF at 80° C. This afforded the corresponding 6,6'-diazide 20, which was conjugated to the alkyne 9 using similar conditions as above to afford the desired conjugate 21. After sequential deprotection steps as described above, the pure sucrose-based ligand 21 was obtained by gel filtration on Sephadex LH-20.

Figure 4A:
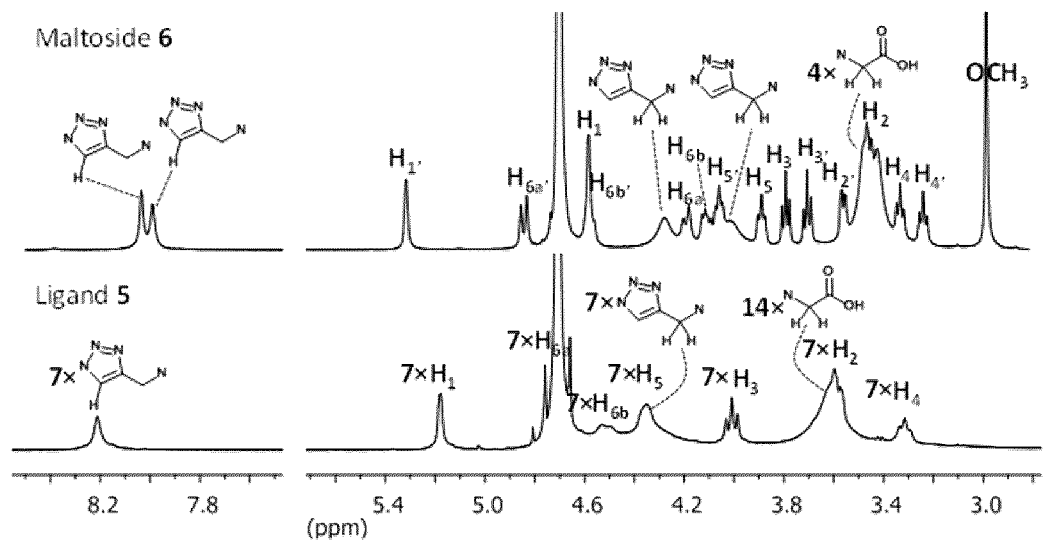
FIG. 4A shows $^1$H NMR spectra of compound 5 and compound 6 (600 MHz, D$_2$O, 25° C.).
Figure 4B:
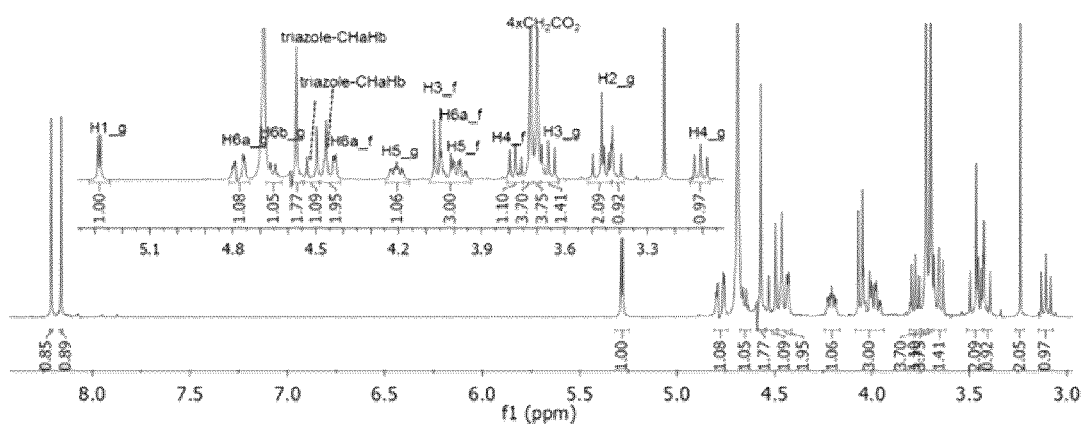
FIG. 4B shows $^1$H NMR spectra of sucrose derivative 22 (400 MHz, D$_2$O, 25° C.).

The structures of both compounds 5 and 6 were confirmed by ESI-HRMS in negative ion mode. For instance, for compound 5, a triply charged ion was observed at m/z 834.5876, which corresponds to the expected formula: $C_{91}H_{123}N_{28}O_{56}$ $(M-3H)^{3-}$ (calculated m/z: 834.5885). The persubstitution of the compound 5 was confirmed by the observed axial symmetry in the $^1$H NMR spectrum. For instance, a singlet at 8.21 ppm and a doublet at 5.18 (J=2.8 Hz) were observed, which were assigned to the one set of 1,2,3-triazole protons and anomeric protons respectively (FIG. 4A), found in compound 5. Similarly, for the maltoside-based compound 6, the related ion corresponding to the expected formula $C_{27}H_{39}N_8O_{17}$ (M-H)$^-$ was observed at m/z 747.2422 (calculated m/z: 747.2439). In the $^1$H NMR spectrum of the compound in D$_2$O (FIG. 4A), two singlets related to the 1,2,3-triazole peaks were observed at 8.08 and 8.03 ppm, and two anomeric protons were observed at 5.31 and 4.56 ppm (doublets) respectively, which respectively correspond to the two sets of signals in the molecule. Each of the other types of protons also appeared as two sets of signals. Analogously, the structure of the sucrose ligand 22 was confirmed by ESI-HRMS (negative ion mode). The expected formula $C_{26}H_{37}N_8O_{17}$ (M-H)$^-$ was observed at m/z 733.2295 (calculated m/z: 733.2282); this was further confirmed by the observation of a doubly charged ion at m/z 366.1115, which correspond to the expected formula $C_{26}H_{36}N_8O_{17}$ (M-2H)$^{2-}$ (calculated m/z: 366.1105). In the $^1$H NMR spectrum of the sucrose ligand 22 in D$_2$O (FIG. 4B), two types of 1,2,3-triazole protons were observed at 8.28 and 8.24 ppm, respectively, confirming the presence of two 1,2,3-triazole units. In addition, the anomeric proton of the glucopyranosyl unit was observed at the 5.35 ppm as a doublet, while the H-6a and H-6b of the same unit were observed at 4.78 and 4.67 ppm, respectively. For the fructofuranosyl unit, the H-6a and H-6b were observed at 4.45 and 4.05 ppm respectively. Furthermore, the presence of 2 pairs of N-acetates was confirmed by the two peaks at 3.73 and 3.70 ppm, respectively.

Figure 4C:
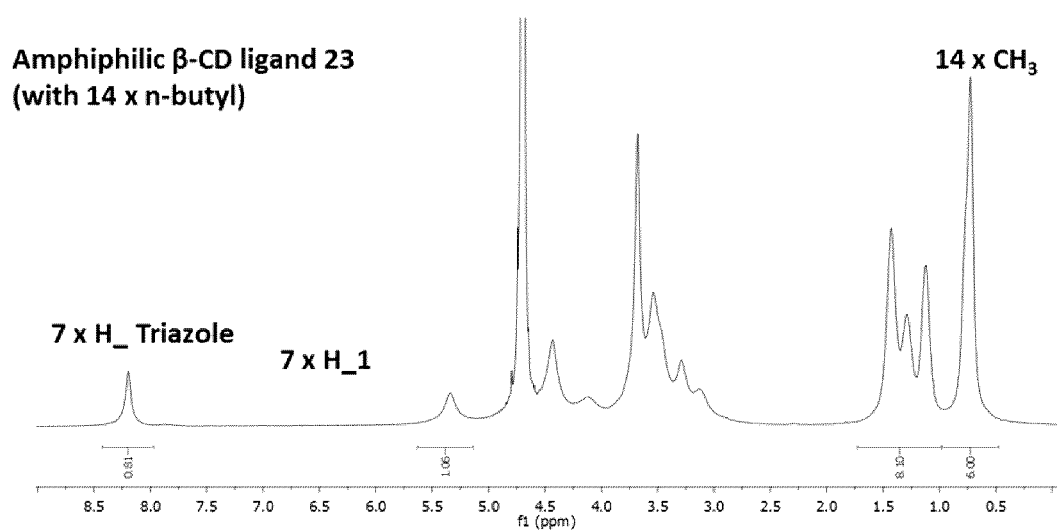
FIG. 4C shows the $^1$H NMR spectrum of amphiphilic b-CD compound 23 (400 MHz, D$_2$O, 25° C.).

The structure of compound 23 was also confirmed by $^1$H-NMR spectrometry, as shown in FIG. 4C. The proton signals are generally broad in D$_2$O, suggesting the formation of aggregates in solution. The identity of compound 23 was further confirmed by high resolution mass spectrometry (negative electrospray), which showed the expected triple-charged ion at m/z 1096.2095, corresponding to the expected molecular formula of $C_{147}H_{235}N_{28}O_{56}$ (M-3H)$^{3-}$ (calculated m/z: 1096.2039).

Protonation of Compound 5

Figure 5:
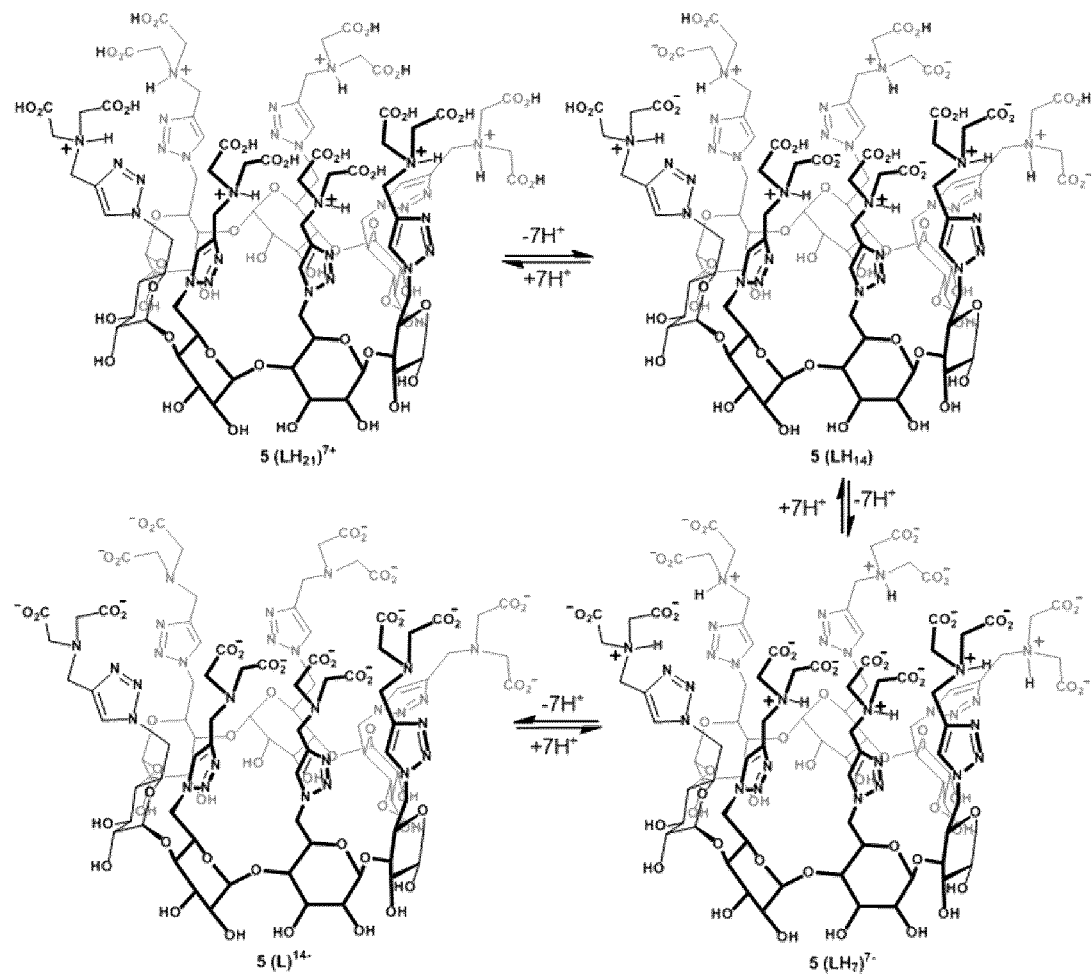
FIG. 5 illustrates examples of stepwise protonation states of compound 5.

Compound 5 contains numerous protonation sites, including 14 carboxylates, 7 tertiary amines and 7 1,2,3-triazole rings (see FIG. 5). Based on pKa values of related functional groups such as N-methyl-1,2,3-triazolium (1.25),[34] acetic acid (~4.76), and triethylammonium (~10.75), the protonation of the 1,2,3-triazole rings in the molecule can be ignored since this protonation only becomes relevant at very acidic pH. Thus, in less acidic solutions, compound 5 contains essentially 21 protonation sites, designated as [LH$_{21}$]$^{7+}$; a stepwise deprotonation process would lead to other intermediate stages such as the neutral species LH$_{14}$, the fully deprotonated intermediate from carboxylates [LH$_7$]$^{7-}$ and finally the completely deprotonated ligand L$^{14-}$ from both carboxylate and ammonium functional groups.

In order to gain insight into the involvement of the carboxylates in the coordination with the metal ion, attenuated total reflection (ATR) FTIR studies were performed on compound 5. It is well known that deprotonation of the carboxylic acid would lead to the absence of any strong bands around 1700 cm$^{-1}$ in the IR spectrum; the resulting carboxylate typically has two vibrational modes at around 1600 cm$^{-1}$ and 1400 cm$^{-1}$ due to the symmetric ($v_{s\_COO}$) and antisymmetric ($v_{as\_COO}$) modes. The ATR-FTIR spectrum of compound 5 has two stretching bands at 1619.7 cm$^{-1}$ and 1396.1 cm$^{-1}$ (not shown), indicating that the carboxylates of the isolated compound 5 were indeed fully deprotonated.

Figure 6:
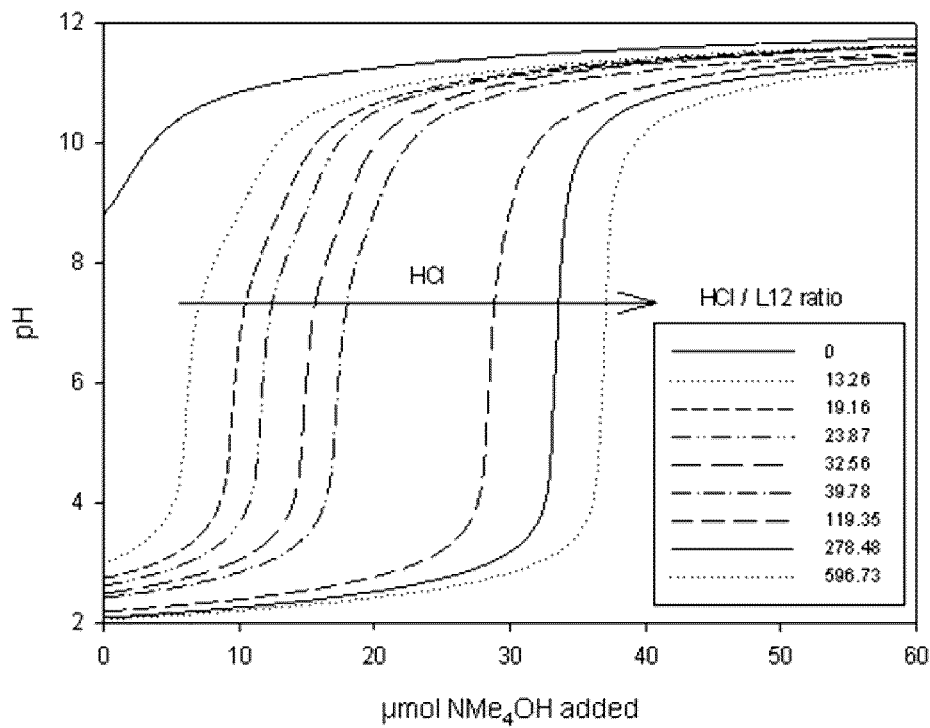
FIG. 6 shows the results of potentiometric titrations of compound 5. T=298K, [L]=0.0625-1 μmol, [extra-HCl]=0-37.3 μmol in NMe$_4$Cl (0.1 M); total initial volume: 4 mL; burette: [NMe$_4$OH]=0.05 M.
Figure 7:
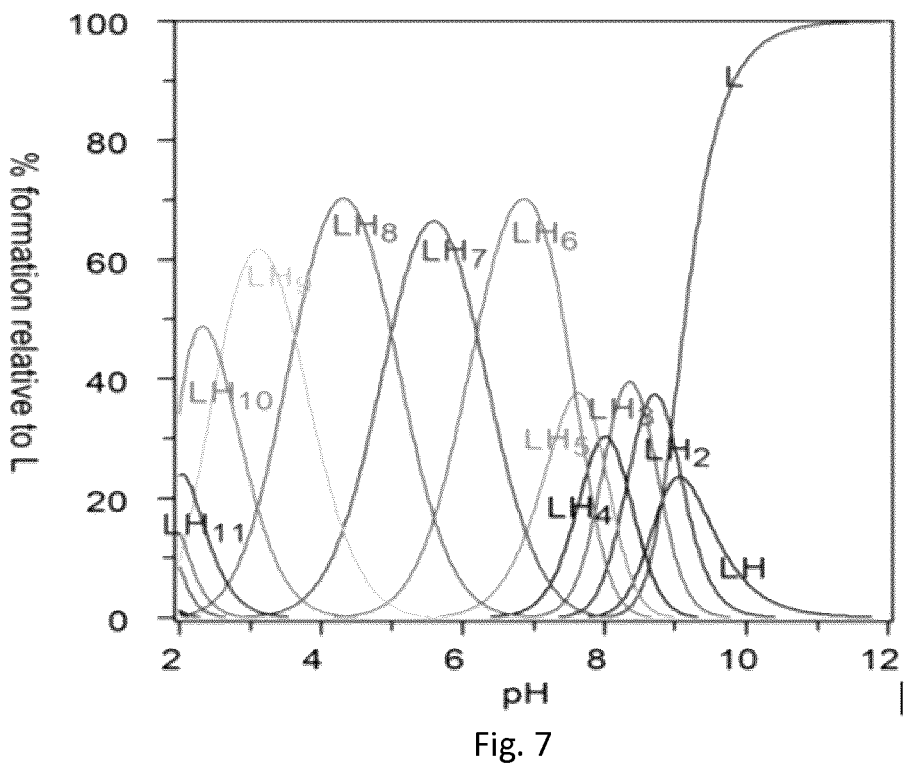
FIG. 7 shows the calculated distributions of different protonated species at different pH values.

Potentiometric titrations were performed to study the deprotonation of compound 5 (FIG. 6). The initial solution of compound 5 alone has a pH of ~8.4; this value correlates well with extensive deprotonation observed in ATR-FTIR spectrum. Therefore, a solution of HCl in trimethylammonium chloride (0.1 M) was gradually added to the solution to obtain a series of solutions with varied HCl/5 ratios (0→597), while maintaining the total volume constant. To each prepared solution, a titrant solution of tetramethylammonium hydroxide (0.05 M) was added while the pH of the solution recorded; this enabled preparation of a series of titration curves (FIG. 7). As can be seen, with increasing HCl/5 ratios, the form of the obtained curves becomes increasingly similar to that of pure HCl, while with decreasing HCl/5 ratios, the form of the curves becomes more representative of compound 5.

The protonation constant $\beta_h$ for the following equilibrium is defined by equation 1, where L represents the fully deprotonated form (L$^{14-}$) of compound 5 (LH$_{14}$). H is the proton (charges are omitted).

$$L + hH \rightleftharpoons LH_h; \quad \beta_h = \frac{[LH_h]}{[H]^h[L]} \quad \text{(equation 1)}$$

As dissociation constants $K_a$ are commonly defined by:

$$K_a = \frac{[H][LH_{h-1}]}{[LH_h]} \quad \text{(equation 2)}$$

it is evident that $$K_a = \log \beta_h - \log \beta_{h-1} \quad \text{(equation 3)}$$

it is evident that $$K_a = \log \beta_h - \log \beta_{h-1} \quad \text{(equation 3)}$$

Table 1 reports all protonation constants determined by titration curve refinement and the corresponding acidity constants. All pKa values were ascribed to successive deprotonation of the carboxylic acids, followed by ammonium functions.

TABLE 1

Stepwise Protonation Constants of Compound 5

| Species | log $\beta_{LHh}$ | pKa |
|---|---|---|
| LH | 8.80 | |
| LH$_2$ | 17.77 | 9.08 |
| LH$_3$ | 26.44 | 8.56 |
| LH$_4$ | 34.51 | 8.07 |
| LH$_5$ | 42.44 | 7.93 |
| LH$_6$ | 50.03 | 7.59 |
| LH$_7$ | 56.23 | 6.20 |
| LH$_8$ | 61.22 | 4.99 |
| LH$_9$ | 64.85 | 3.63 |
| LH$_{10}$ | 67.42 | 2.57 |
| LH$_{11}$-LH$_{21}$ | N/A | <2 |

(Charges are omitted)

As can be seen from Table 1, a pKa of 6.20 was determined to be near the neutral pH. Based on the known pKas of ammonium and carboxylic acid functional groups, this pKa could be ascribed to the [LH$_7$]$^{7-}$ species. The pKas lower than 6.20 could be assigned to carboxylic acid moieties while pKas over 6.20 could be attributed to ammonium moieties. Thus, the major species in the solution of neutral pH should correspond to the species with complete deprotonation of carboxylic acids while the first ammonium group is not yet totally deprotonated [LH$_6$]$^{8-}$ (pKa~7.59), which exists in equilibrium with [LH$_7$]$^{7-}$ (pKa~6.20) and [LH$_5$]$^{9-}$ (pKa~7.93). More alkaline solutions revealed two additional pKas at 8.07, 8.56, 9.08 and 8.80 which were assigned to [LH$_4$]$^{10-}$ and [LH$_3$]$^{11-}$, [LH$_3$]$^{12-}$, and [LH$_3$]$^{13-}$ respectively. Normally, the successive pKa values of the Brönsted pairs increase according to the successive dissociation into a polyprotic acid. Nevertheless, the delta pKa values of the pairs [LH2]$^{12-}$/[LH]$^{13-}$, [LH3]$^{11-}$/[LH2]$^{12-}$, [LH4]$^{10-}$/[LH3]$^{11-}$ and [LH5]$^{9-}$/[LH4]$^{10-}$ differ from a "statistical factor" pKn+1−pKn=0.6, which suggests that the involved dissociable groups are interacting with each other.

On the other hand, in more acidic solutions, three pKas were determined at 4.99, 3.63, 2.57, which were assigned to be the sequential protonated species from [LH$_7$]$^{7-}$, namely [LH$_8$]$^{6-}$, [LH$_9$]$^{5-}$ and [LH$_{10}$]$^{4-}$ respectively. The determined pKas undergo a rapid decrease from 6.20 to 2.57, as each successive protonation produces less negatively charged carboxylates, reducing charge-charge repulsion between adjacent carboxylates. The pKas corresponding to highly protonated species ranging from [LH$_{11}$]$^{3-}$ to [LH$_{21}$]$^{7+}$ were found to be lower than pH 2, which is too low to allow accurate determination.

Based on the determined pKas, a diagram of percentage distributions of different protonated species according to pH, is shown in FIG. 7.

MTT Assays of Compound 5

Figure 8:
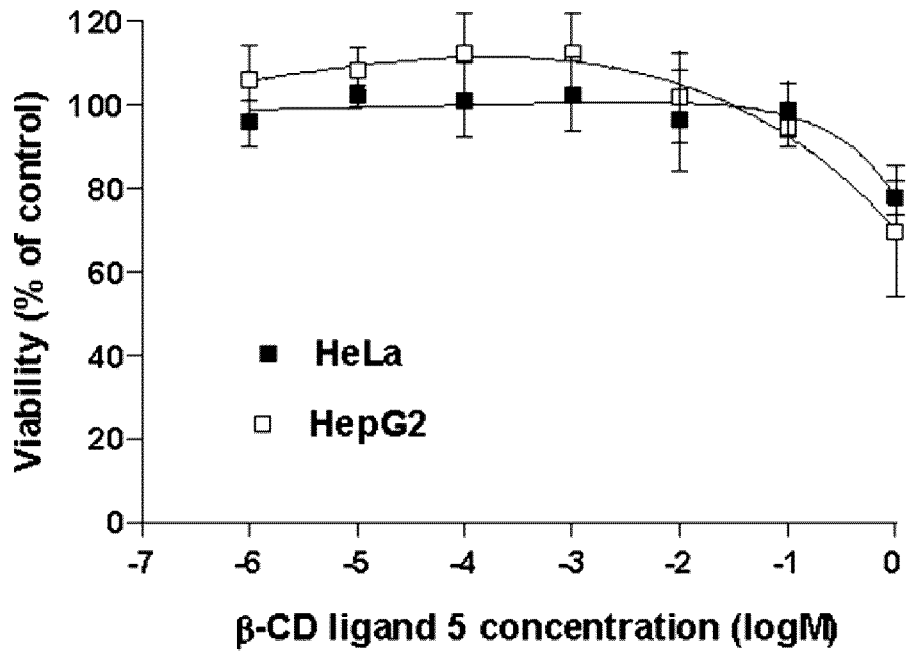
FIG. 8 shows the results of in vitro cytotoxicity assays (MTT) of compound 5 in HeLa and HepG2 cell lines.

The in vitro cytotoxic effect of compound 5 was analyzed using HeLa and HepG2 cells in MTT assays.[35] Both cell lines showed a slight cytotoxic effect (20-40% inhibition) at concentrations higher than 1 mM, suggesting that compound 5 is relatively non-toxic (FIG. 8).

Complexation of Gd(III) with Compounds 5 and 6

Figure 9:
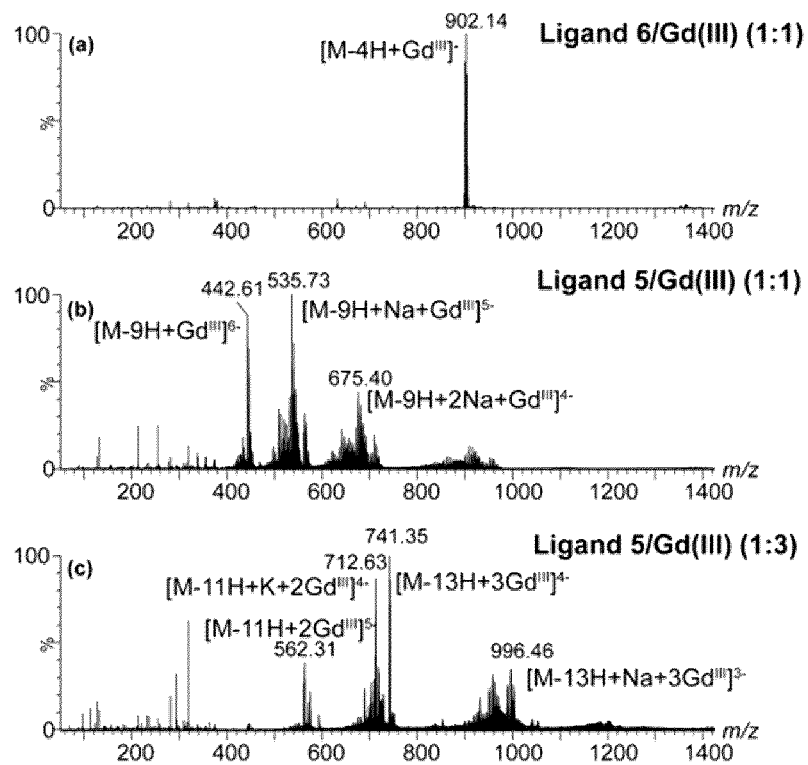
FIG. 9 shows ESI-QTOF-MS (negative ion mode) spectra of (a) compound 6 complex 6/Gd(III) (1:1); (b) a mononuclear compound 5 complex 5/Gd(III) (1:1); and (c) a mixture of mononuclear (1:1), dinuclear (1:2) and trinuclear (1:3) complexes 5/Gd(III).

Addition of GdCl$_3$ to a solution of either compound 5 or 6 led to the formation of Gd(III)-complexes. In case of compound 6, when one equivalent of GdCl$_3$ was added, only 1:1 compound 6/Gd(III) complex was detected by ESI-MS in negative ion mode (FIG. 9a), since the main ion is observed at m/z 902.14 and corresponds to singly charged ion [M-4H+Gd(III)]—(C$_{27}$H$_{36}$N$_8$O$_{17}$Gd)$^-$ (m/z found: 902.1442, calculated: 902.1446). Similarly, when one equivalent of GdCl$_3$ was added to compound 5, the 1:1 compound 5/Gd(III) complex was observed as the main species in the solution as evidenced by ESI-MS (FIG. 9b). The MS spectrum was found to be rather complex due to the presence of many ions with different charged states and adducts. Ions at m/z 442.6122, 535.7288 and 675.4021 correspond to [M-9H+Gd]$^{6-}$ (C$_{91}$H$_{117}$N$_{28}$O$_{56}$Gd)$^{6-}$, [M-9H+Na+Gd]$^{5-}$ (C$_{91}$H$_{117}$N$_{28}$O$_{56}$NaGd)$^{5-}$ and [M-9H+2Na+Gd]$^{4-}$ (C$_{91}$H$_{117}$N$_{28}$O$_{56}$Na$_2$Gd)$^{4-}$ species respectively. On the other hand, when more than one equivalent of GdCl$_3$ was mixed with compound 5, the other multinuclear complexes were gradually detected. As an example, when three equivalents of GdCl$_3$ were added, the ESI-MS spectrum revealed the presence of mainly dinuclear ([M-11H+2Gd]$^{5-}$; [M-11H+K+2Gd]$^{4-}$) and trinuclear ([M-13H+3Gd]$^{4-}$; [M-13H+Na+3Gd]$^{3-}$) species (FIG. 9c).

The Gd(III) complexes with compounds 5 and 6, were found to be extensively deprotonated. For example, the Gd(III) complex of compound 6 was found to be fully deprotonated, suggesting that both the amines and all the four carboxylates are available to coordinate to Gd(III). For the Gd(III)-complexes of compound 5, the HRMS spectra revealed a loss of 9 protons, while for dinuclear and trinuclear complexes, the HRMS spectra revealed further loss of 11 and 13 protons respectively. In all these cases, it can be concluded that there are at least two free amines and four carboxylates available for each Gd(III), as in the case of complex of compound 6/Gd(III).

To further characterize the coordination sphere of formed Gd(III) complexes, $^1$H NMR titrations were performed to study the complexation of both compounds 5 and 6 with the diamagnetic yttrium(III) chloride). It is known that both Gd(III) and Y(III) have similar coordination spheres.[36]

Figure 10A:
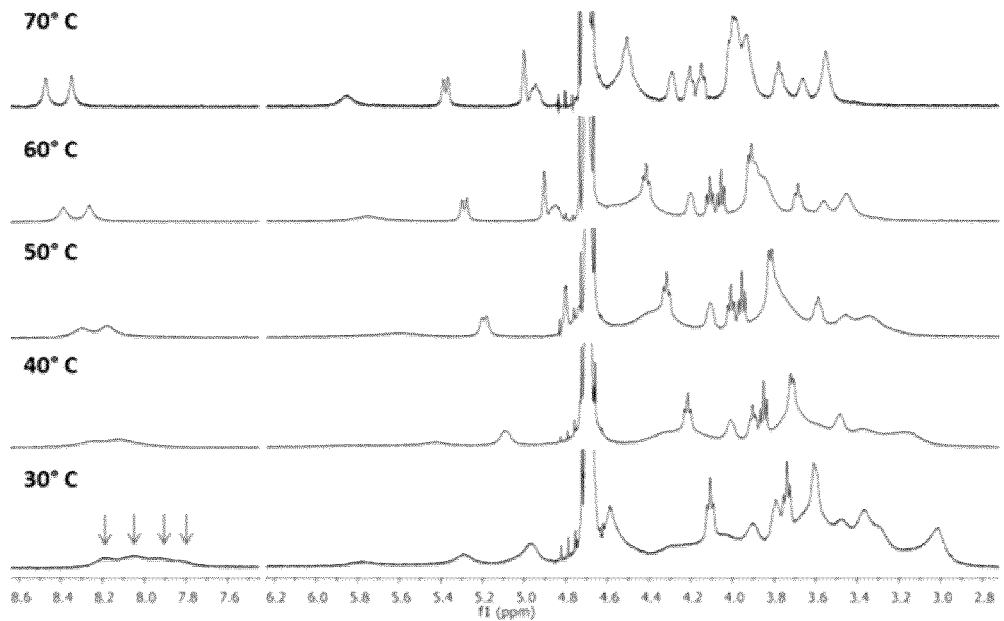
FIG. 10A shows the results of variable temperature $^1$H NMR experiments (30 to 70° C., D$_2$O, 600 MHz) of a sample containing 1:1 Y(III)/compound 6 (14 mM) in D$_2$O.

Thus, using the simplified compound 6 as a model, a series of NMR titration experiments were carried out in deuterium oxide at 25° C., by adding a solution a solution of Y(III) chloride in the same solvent (FIG. 10A).

Figure 11:
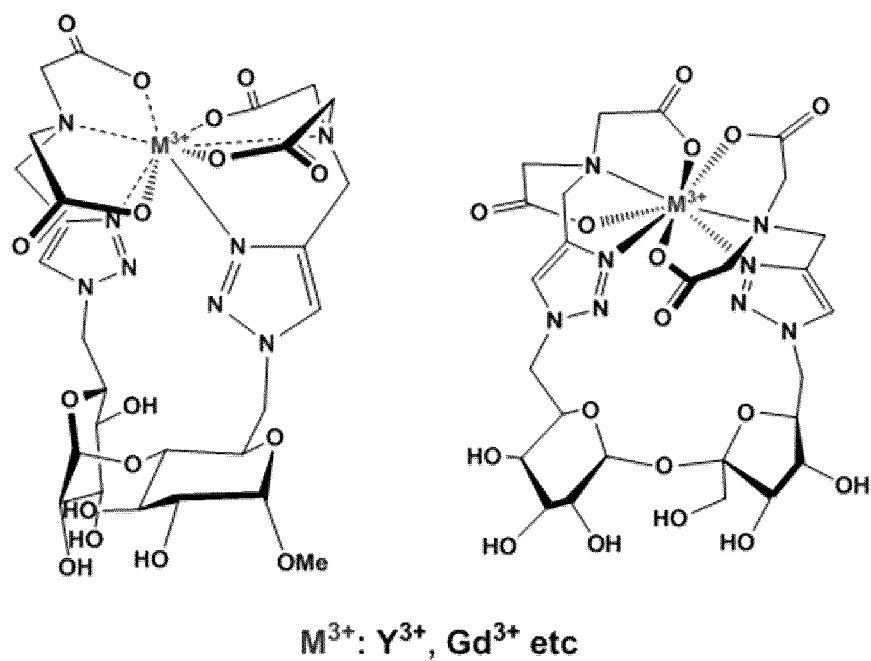
FIG. 11 is a proposed model of coordination in the complexes of compound 6 and compound 5 with lanthanides such as Y(III) and Gd(III). The two adjacent iminodiacetate and 1,2,3-triazole units provide an octavalent coordination sphere for the metal center.

It is seen that with the addition of 0.25-0.75 equivalent of the Y(III) chloride, the $^1$H NMR spectra of the sample experiences a dramatic change within the regions of the 1,2,3-triazole protons, the 2 pairs of methylene protons (3.98 and 4.26 ppm) attached to the 1,2,3-triazole, as well as the methylene protons of the N-acetates (~3.5 ppm). This contrasts with the two anomeric protons (~5.3 ppm, 4.55 ppm) and anomeric methyl group (2.94 ppm), which only showed slight shifts during the titrations. When the amount of Y(III) was increased to ~1 equivalent and above, no further significant changes in the $^1$H NMR spectra were observed, confirming the 1:1 stoichiometry observed from mass spectrometry. The significant changes in chemical shifts of all methylene groups mentioned above are expected, as they are almost certainly involved in the coordination with metal. The very significant changes in chemical shifts of the two types of 1,2,3-triazole rings strongly suggested their direct involvement in metal chelation. Indeed, the participation of two 1,2,3-triazole rings in coordination combined with the two adjacent iminodiacetates provides an octavalent coordination sphere to the metal center (FIG. 11).

Figure 10B:
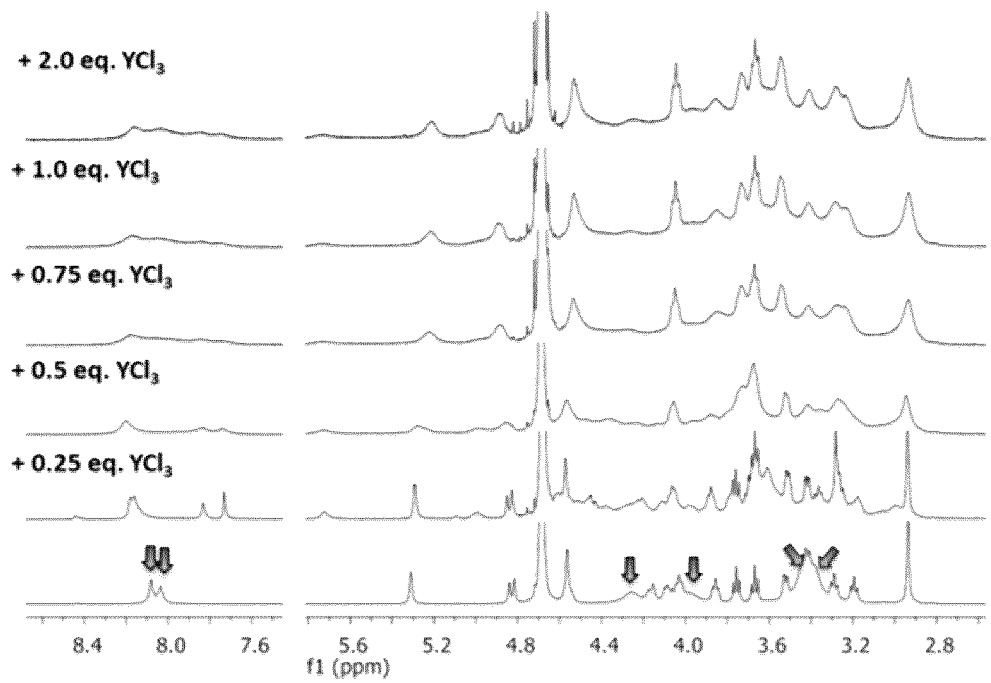
FIG. 10B shows the results of an NMR titration (D$_2$O, 25° C., 600 MHz) of a solution of compound 6 with Y(III) chloride.

Additionally, it was noted that the two types of 1,2,3-triazole protons signals split into two sets of signals (8.16/8.03 ppm vs 7.84/7.73 ppm), suggesting that the 1:1 compound 6/Y(III) complex might in fact exist in two conformations in solution. To confirm this, a variable temperature experiment was carried out by gradually heating an NMR sample containing 1:1 ratio of YCl$_3$/compound 6 in D$_2$O from 30 to 70° C. (FIG. 10B). It is seen that when the temperature is raised to 40° C., the four broad peaks of 1,2,3-triazole signals gradually shift into two broad singlets that continue to be better resolved at higher temperatures. At 70° C., the two singlets became completely resolved and the spectrum becomes much more simplified, suggesting that faster conformational exchange occurs at higher temperatures.

Analogously, $^1$H NMR titration experiments were carried out on compound 5 by varying the amounts of Y(III) chloride from 0.25 to 4 equivalents. As expected, the NMR spectra are far more complex than the spectrum of the analogous complex of compound 6. The signals are generally very broad and overlap due to the formation of different multinuclear complexes as well as different conformations. This presented considerable difficulties in carrying out full analysis of the spectra. However, similar to what was observed with the complex of compound 6, significant changes in chemical shifts on protons related to the 1,2,3-triazole rings were observed as well as the three types of methylene protons found in compound 5. Since HRMS experiments confirmed that compound 5 is capable of complexing up to three transition metals, it was concluded that compound 5 most likely chelates the metal in a similar manner as compound 6 (FIG. 11), where each metal center likely involves two 1,2,3-triazoles and two iminodiacetates attached to adjacent glucopyranosyl units of the β-cyclodextrin. The observed three metal coordination centers would completely engage the chelating groups of the 6 glucopyranosyl units; leaving the chelating groups in the 7th unit not engaged in binding, or available for new functionalization. Although in theory, the chelating groups attached to two diagonally positioned glucopyranosyl units (such as 6A, 6D) of the β-cyclodextrin could engage to form a complex with a single Gd(III) ion. This does not appear to be viable as molecular modeling showed such mode of complexation would introduce considerable torsional stains that lead to significant distortion of the cyclodextrin macrocycle, due to large distance between chelating groups attached to the two opposing glucopyranosyl units. Effective complexation with Gd(III) would require having the chelating groups closer together.

Determination of Formation Constants of Compound 5 with Gd(III)

Figure 12A:
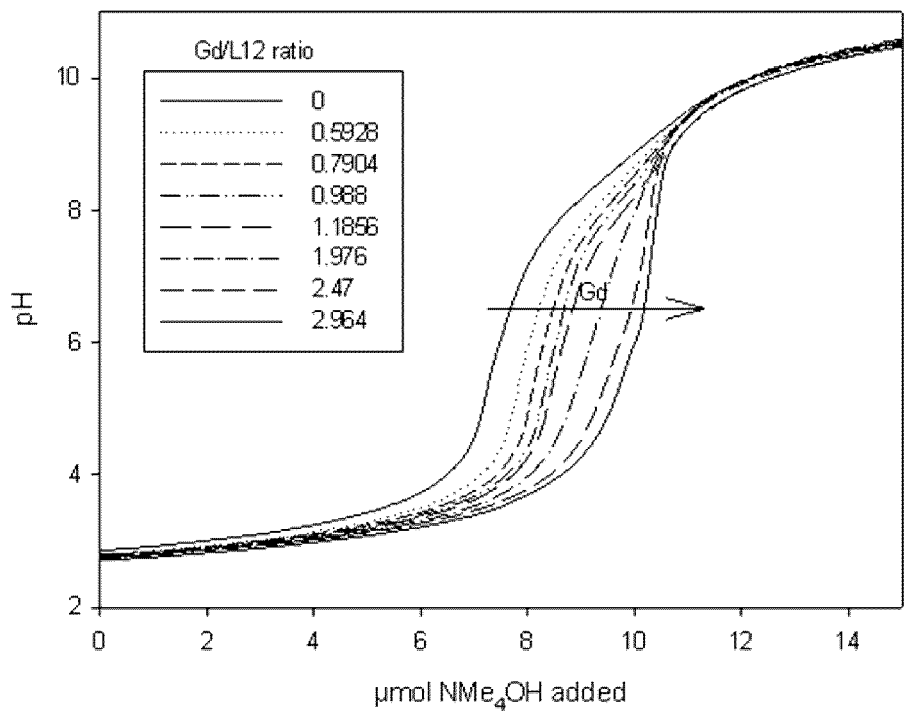
FIG. 12A shows results of potentiometric titrations of Gd(III) (top) with [L]=0.5 μmol; [extra-HCl]=9.9456 μmol in NMe$_4$Cl$_1$ (0.1 M), total initial volume: 4 mL and burette: [NMe$_4$OH]=0.05 M. Distribution curves of with [extra-HCl]=9.9456 μmol in NMe$_4$Cl (0.1 M), total initial volume: 4 mL. Considering the collection of results obtained for the Gd(III)-compound 5, the best chemical model which fits the data corresponds to: (1) mononuclear GdL species for Gd:L ratio lower than 1, (2) binuclear species Gd2L for Gd:L ratio higher than 1 or (3) trinuclear species Gd3L for Gd:L ratio higher than 2.

The complexation of compound 5 with Gd(III) was studied by potentiometric titrations. While maintaining the amount of compound 5 (0.5 μmol) and HCl (9.95 μmol) constant within the cell, a solution of GdCl$_3$ was then added to reach a specified ratio. This solution was then titrated with tetramethylammonium hydroxide (NMe$_4$OH). It was noted that with the solution containing the highest Gd:L ratios, the addition of same amount of base caused a slower increase of pH (FIG. 12A). This could be explained by the displacement of protons from the protonated groups during Gd(III) complexation, thus acidifying the medium.

The GdL complex was formed over pH 7-8, when all carboxylate groups were deprotonated. The other successive protonations could be attributed to other ammonium sites protonated while not coordinated to Gd(III). Example: GdLH$_4$: refers to Gd complex with four protonated and three deprotonated ammonium groups.

The distribution curves underline that at neutral pH, GdLH$_3$ (below 60%) is in equilibrium with GdLH$_4$ and GdLH$_2$ (both just above 20%) in case of 1:1 Gd:L ratio. Gd$_2$LH$_2$ and Gd$_2$LH correspond to the major species in case of 2:1 Gd:L ratio and in equilibrium with Gd3LH and Gd3L in case of 3:1 Gd:L ratio.

The stability constants of the Gd(III) complexes are expressed by the general formula:

$$mM + lL + hH \rightleftharpoons M_mL_lH_h; \quad \beta_h = \frac{[M_mL_lH_h]}{[M]^m[L]^l[H]^h} \quad \text{(equation 4)}$$

with M being the metal ion, L the ligand, and H the proton (the charges are omitted), and dissociation constant $K_{mlh}$ can be defined similarly to the case of free ligand as:

$$K_{mlh} = \frac{[H][M_mL_lH_{h-1}]}{[M_mL_lH_h]} \quad \text{(equation 5)}$$

Analogously, $$pK_{mlh} = \log\beta_{mlh} - \log\beta_{mlh-1} \quad \text{(equation 6)}$$

Analogously, $$pK_{mlh} = \log\beta_{mlh} - \log\beta_{mlh-1} \quad \text{(equation 6)}$$

Figure 12B:
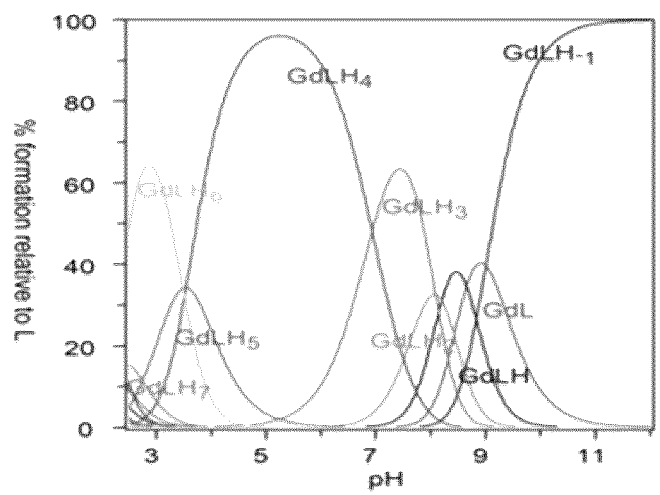
FIG. 12B is a plot indicating formation of the 1:1 complex with [Gd]=[L]=0.5 μmol.
Figure 12C:
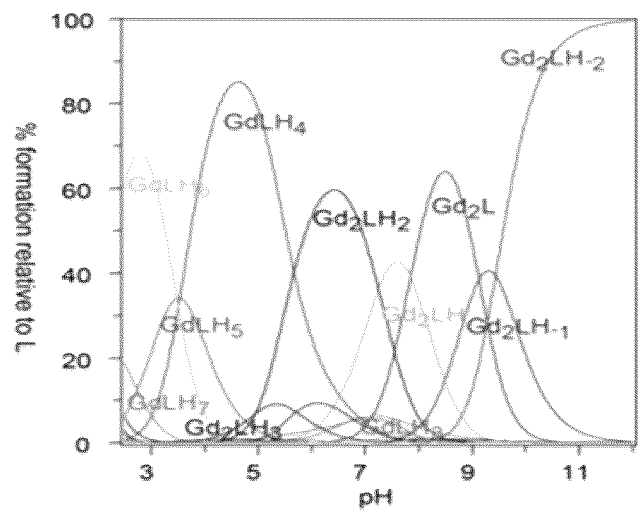
FIG. 12C is a plot indicating formation of the 2:1 complex with [Gd]=2×[L]=0.5 μmol.
Figure 12D:
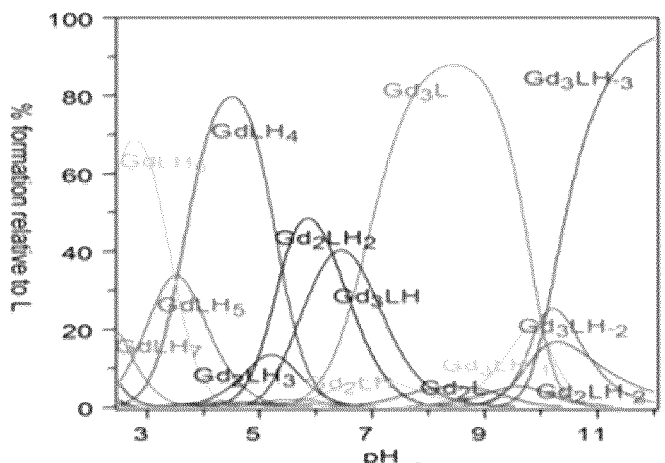
FIG. 12D is a plot indicating formation of the 3:1 complex with [Gd]=3×[L]=0.5 μmol.

The stability constants of the Gd(III) complexes are reported in the Table 2 and distribution curves given in FIGS. 12B, 12C and 12D, respectively for 1:1, 2:1 and 3:1 Gd(III):compound 5 ratios.

TABLE 2

Stepwise Protonation Constants of Gd(III)-Compound 5 Complexes

| Species | MLH | log $\beta_{MLHh}$ | pKa |
|---|---|---|---|
| Mononuclear | | | |
| GdLH$_{-1}$ | 11-1 | 16.08 | — |
| GdL | 110 | 25.09 | 9.01 |
| GdLH | 111 | 33.74 | 8.55 |
| GdLH$_2$ | 112 | 41.95 | 8.21 |
| GdLH$_3$ | 113 | 50.04 | 8.09 |
| GdLH$_4$ | 114 | 56.97 | 6.93 |
| GdLH$_5$ | 115 | 60.51 | 3.54 |
| GdLH$_6$ | 116 | 64.00 | 3.49 |
| Following | | | <2.5 |
| Dinuclear | | | |
| Gd$_2$LH$_{-2}$ | 22-2 | 17.71 | — |
| Gd$_2$LH$_{-1}$ | 22-1 | 27.15 | 9.44 |
| Gd$_2$L | 210 | 36.28 | 9.13 |
| Gd$_2$LH | 211 | 43.13 | 7.85 |
| Gd$_2$LH$_2$ | 212 | 51.38 | 7.25 |
| Gd$_2$LH$_3$ | 213 | 56.33 | 4.95 |
| Gd$_2$LH$_4$ | 214 | 60.27 | 3.94 |
| Gd$_2$LH$_5$ | 215 | 63.54 | 3.27 |
| Gd$_2$LH$_6$ | 216 | 66.45 | 2.95 |
| Following | | | <2.5 |
| Trinuclear | | | |
| Gd$_3$LH$_{-3}$ | 31-3 | 13.80 | — |
| Gd$_3$LH$_{-2}$ | 31-2 | 23.91 | 10.10 |
| Gd$_3$LH$_{-1}$ | 31-1 | 33.83 | 9.92 |
| Gd$_3$L | 310 | 43.91 | 10.10 |
| Gd$_3$LH | 311 | 50.70 | 6.79 |
| Gd$_3$LH$_2$ | 312 | 55.36 | 4.66 |
| Gd$_3$LH$_3$ | 313 | 60.09 | 4.73 |
| Gd$_3$LH$_4$ | 314 | 64.99 | 4.90 |
| Following | | | <2.5 |

(Charges are omitted)

As the water coordination number was about 1 (see next paragraph), speciation forms, which take into account one water molecule in the coordination sphere were considered with their associated hydroxylated forms GdLH$_{-1}$, Gd$_2$LH$_{-1}$, Gd$_2$LH$_{-2}$, Gd$_3$LH$_{-1}$, Gd$_3$LH$_{-2}$, Gd$_3$LH$_{-3}$.

The GdL complex was formed at pH 9, when all carboxylate sites were deprotonated. The other successive protonations could be attributed to other ammonium sites protonated while not coordinated to gadolinium. Example: GdLH$_4$: refers to Gd complex with four protonated and three deprotonated ammonium groups.

The distribution curves clearly show that the metal ion was totally complexed at pH 2.5. They underline that at neutral pH, GdLH$_3$ (~63%) is in equilibrium with GdLH$_4$ and GdLH$_2$ (~18.5%) in case of 1:1 Gd:L ratio. Gd$_2$LH (~40%) is in equilibrium with Gd$_2$LH$_2$ (~30%) and Gd$_2$L (~15%) in case of 2:1 Gd:L ratio. Gd$_3$L (~67%) is in equilibrium with Gd$_3$LH (~18%) and Gd$_2$LH (~5%) in case of 3:1 Gd:L ratio.

The formation constant (Log K$_{Gd.5}$) for the monometallic complex is on the order of 25. These complexes are remarkably more stable than those described for the native cyclodextrin (log Gd=2.5),[37] even several orders of magnitudes higher than the values of some strong aminocarboxylate ligands such as EDTA (log βGd=17.7) and DTPA (log βGd=22.5), and in fact its stability is comparable to DOTA (log βGd=25.3), which is the strongest complex currently available on the market. To the best of the inventors' knowledge, it is also the best of the known chemically-modified ligands for Gd(III) based on cyclodextrin scaffolds without relying on DTPA or DOTA. Nevertheless, the thermodynamic stability of gadolinium complexes can't be considered as the only parameter to study the toxicity of gadolinium complexes. Effectively, the release of highly toxic Gd(III) in vivo is also important because endogenous metal ions, such as Zn(II), Fe(II), Cu(II) and Ca(II) are able to replace Gd(III) in the complexes. Therefore, the inertness of the complexes is under investigation.

Compound 5 allows the complexation of a secondary metallic cation with a formation constant of 36.28 in case of the Gd$_2$L species. The introduction of this second cation is more difficult (log βGd (210)–log βGd (110)=11.19), certainly due to electrostatic repulsions. A similar conclusion can be reached by comparing log βGd (310) with log βGd (210). Effectively, log βGd (310)–log βGd (210)=7.63.

The pM value reveals the concentration of free metal ion left uncomplexed by the ligand; thus, it provides a more complete picture of the effectiveness of the ligand in chelating the metal centre. The variation of pGd with pH for a particular Gd(III) complex can give useful information about the stability of the complex under different pH conditions. The pGd[38] has been calculated as a function of pH for a standard set of conditions (initial concentration: [Gd]=1 mM, [L]=10 mM) where: pGd=–log [Gd]$_{free}$. pGd value needs to be as high as possible to ensure negligible dissociation, as Gd(III) is toxic.

Figure 13:
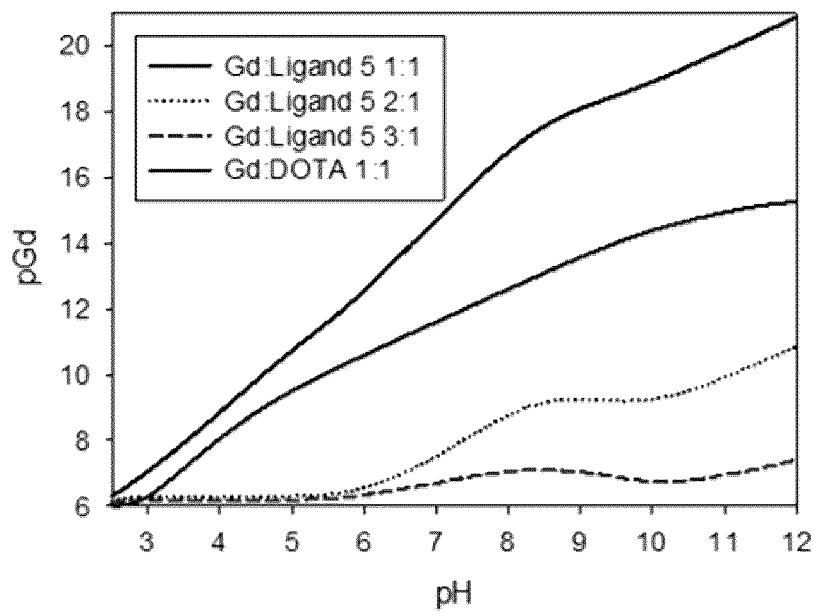
FIG. 13 is a plot of pGd value of compound 5-Gd complexes as a function of pH. ([Gd]$_{total}$=1 μM and [compound 5]$_{total}$=10 μM).

In the case of the ligand 5-Gd complex, as shown in FIG. 13, the maximum pGd value (~31) was obtained at pH 12. At pH 7.4 which is equivalent to physiological media, the measured pGd is 23. This value is significantly higher than the pGd values taken from the literature for Gd-DTPA (19.1) and Gd-DOTA (18.9) complexes.[39] It is clear that this ligand 5-Gd complex is more stable than the Gd-DTPA and Gd DOTA complexes. This result clearly illustrates the undiscovered potential of using CD scaffolds to design high affinity ligands for metal complexation by taking advantage of the cooperativity effect of chelating groups introduced to the macrocycles. But, as explained before, kinetic inertness remains to be evaluated to study transmetallation.

Water Coordination Number

The hydration number was determined using the well-established luminescence method on the corresponding Eu$^{3+}$ complexes of compound 5. Thus, by preparing the complexes in H$_2$O and D$_2$O, and measuring the time resolved luminescence, the water coordination number (q) was calculated from the following equation based on the well-established isotope effect of the Eu$^{3+}$ complexes:

$$q = t \times (1/\tau_{H2O} - 1/\tau_{D2O} - k_{corr}) \quad \text{(equation 7)}$$

where t and k$_{corr}$ represent a constant in each case, which depend on the lanthanide used; in the case of Eu$^{3+}$, where t and the correction factor k$_{corr}$ are constants depending on the types of relation used; in the case of Parker's relationship, t=1.2 ms$^{-1}$ and k$_{corr}$=–0.25 ms, and in the case of the Supkowski-Horrocks relationship, t=1.11 ms$^{-1}$ and k$_{corr}$=–0.31.[40] τH$_2$O and τD$_2$O are the measured luminescence lifetimes of compound 5/Eu$^{3+}$ complexes. The obtained water coordination numbers q$^1$ or q$^2$ based on Parker's relationship and the Supkowsi-Horrocks relationship are reported in Table 3.

TABLE 3

Determination of Water Coordination Number ($q^1$ or $q^2$) Through Time-Resolved Luminescence Measurements of Compound 5/Eu$^{3+}$ Complexes

| Complex | $\tau_{H2O}$ (ms) | $\tau_{D2O}$ (ms) | $q^1$ | $q^2$ |
|---|---|---|---|---|
| 5:Eu-1:1 | 0.621 | 2.582 | 1.168 | 1.013 |
| 5:Eu-1:2 | 0.635 | 2.329 | 1.074 | 0.927 |

$q^1$: Parker's relationship;
$q^2$: Supkowsi-Horrocks relationship

Consequently, for a pH value between 6 and 7, q is equal to 1, which is in agreement with speciation results obtained by potentiometry for a 1:1 complex. Unfortunately, the water coordination number for the 1:3 compound 5/Eu(III) complex, could not be measured due to solubility issues.

Figure 14:
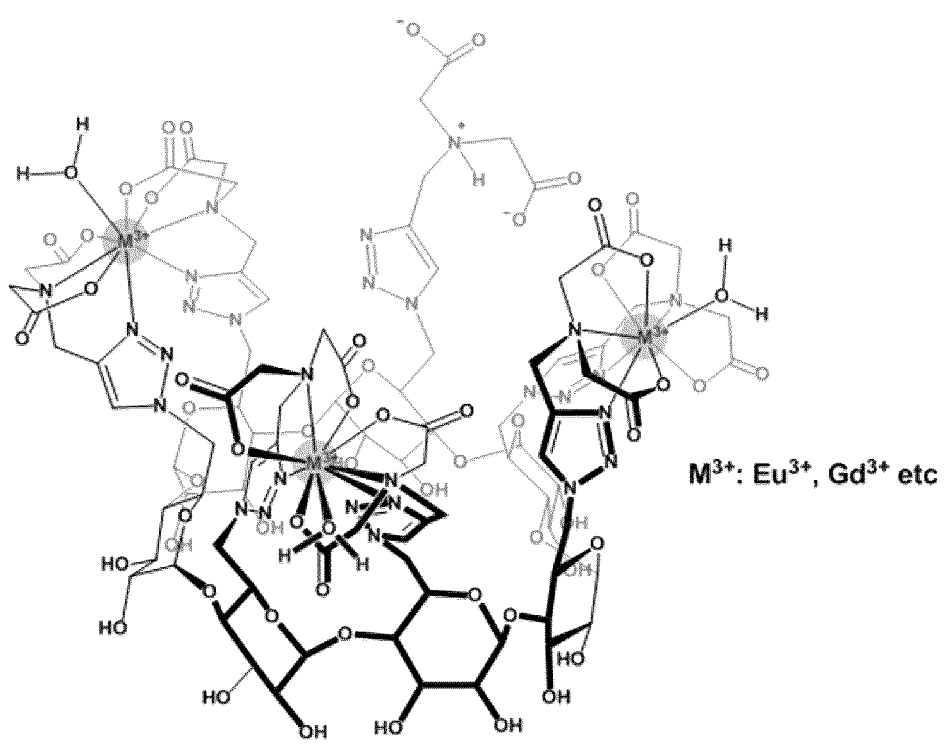
FIG. 14 is a proposed model of octavalent coordination and monohydration in the complexes of compound 5 with 3 bound metal ions.

FIG. 14 shows a model of coordination and monohydration of the multinuclear complex of compound 5 with metal ions. The small, yet rigid 1,2,3-triazole functionalities advantageously displace each metal coordination center away from the primary rim of the β-cyclodextrin so that the iminodiacetate groups can efficiently interact with the metal center with conformations that minimize undesired torsional strains.

Relaxometric Studies

Figure 15:
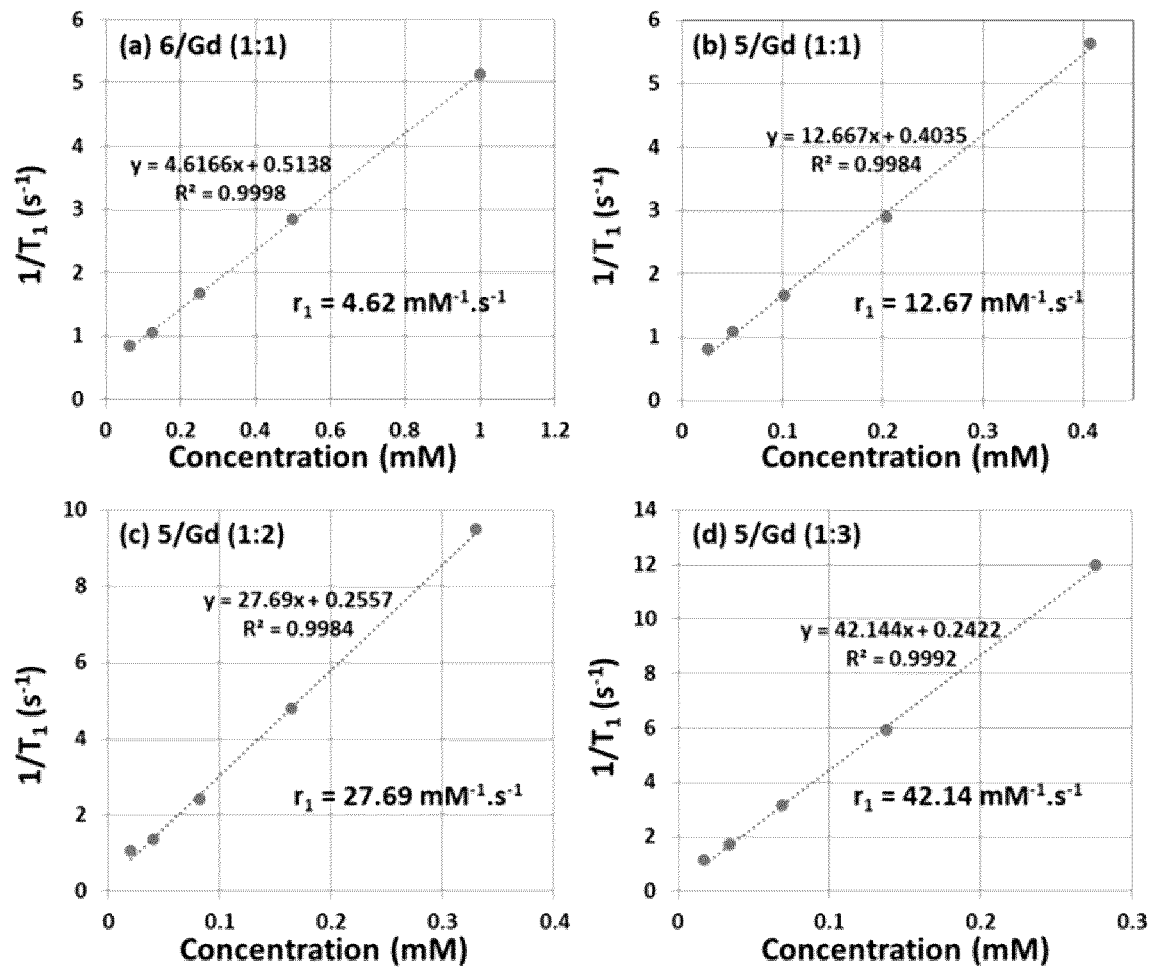
FIG. 15 shows a series of graphs (a) to (d) obtained from relaxivity measurements to confirm the linear relationship between 1/T$_1$ and concentration of compound 6/Gd as well as compound 5/Gd complexes at different ratios.

Relaxivity (T1) measurements were performed with both the compound 6 and compound 5 at 37° C. on a 0.47 T (20 MHz) instrument using the "Inversion Recovery Pulse Sequence." The resulting curves were adjusted to a mono-exponential function to obtain T1. Relaxation values were measured three times and the average was calculated (FIG. 15).

For the 1:1 Gd(III) complex of compound 6, a relaxivity value (r1) of 4.61 mM$^{-1}\cdot$s$^{-1}$ was obtained. For the 1:1, 1:2 and 1:3 compound 5/Gd(III) complexes, relaxivity values of 12.67 mM$^{-1}\cdot$s$^{-1}$, 27.69 mM$^{-1}\cdot$s$^{-1}$ and 42.14 mM$^{-1}\cdot$s$^{-1}$ were obtained respectively. These represent respective increases of 2.7, 4.9 and 9.1 times compared to the compound 6/Gd (III) complex. These values also compare very favorably to the relaxivity of the commercial Gd-DOTA and Gd-DTPA (~3.5-4.3 mM$^{-1}\cdot$s$^{-1}$ at 20 MHz)[1]. Recently, we also measured the relaxivity value (r1) of the 1:1 sucrose ligand 22 Gd(III), which is found to be around 4.5 mM$^{-1}\cdot$s$^{-1}$ which matched the relaxivity of the maltoside 6. Our recently reported per-6-O-acetates of β-cyclodextrin/Gd(III) 4 allowed a relaxivity of 6.53 mM$^{-1}\cdot$s$^{-1}$ (20 MHz)[30] and the ligand 3 was reported to have a relaxivity of 8.8 mM$^{-1}\cdot$s$^{-1}$ (12 MHz)[28] which is lower than the relaxivity of the complexes formed with compound 5. Thus, the advantages of the new compounds 5, 6 and 22 are obvious. Interestingly, some of the recently reported poly-rotaxane-based cyclodextrin-DOTA polymers were reported to have T1 relaxivities in the range of 17.43-23.8 mM$^{-1}\cdot$s$^{-1,20,26}$ which are higher than our 1:2 complex but lower than the 1:3 complex of compound 5/Gd(III), illustrating the great potential of compound 5 for use as an effective MRI contrast reagent.

Contrast Agent Compositions for Magnetic Resonance Imaging

The compounds described herein, exemplified by compounds 5, 6 and 22 complexed to lanthanide ions are reasonably predicted to be useful as contrast agents for magnetic resonance imaging. In preparing contrast agent compositions, various vehicles, excipients, can be utilized. Aqueous vehicles, water-miscible vehicles, or non-aqueous vehicles may be employed. Typically, the formulations for intravenous injection are prepared in an aqueous vehicle, e.g. water for injection, and may optionally contain further excipients known in the art. Various solutes may be added for the purposes of enhancing solubility, patient comfort, chemical stability, and to preserve the preparation. Steps can be taken to remove or destroy pyrogens. Optional added substances can include buffers, antimicrobial agents, antioxidants, etc. Other excipients may include those excipients used in gadolinium based contrast agent formulations. These excipients include those which may serve to stabilize the gadolinium chelate such as various calcium excipients such as caldiamide sodium[41] and calcium hydroxide, calcium chloride dihydrate.[42] Various calcium or zinc salts of the calcium of zinc salt of an organic ligand may be utilized such as those disclosed in U.S. Pat. No. 7,385,041, which is incorporated herein by reference in its entirety. Excipients can also include meglumine, and trometamol (tromethamine). Various surfactants may optionally be employed, particularly for use with water-miscible vehicles, or non-aqueous vehicles. Sodium hydroxide and/or hydrochloric acid may be used to adjust the pH from about pH 5.5 to about pH 8.

Administration of Contrast Agent Compositions

The mode of administration, the dosage and frequency of dosage is governed by the mode of administration and dosage considerations conventionally employed with the contrast agent. Typically, these agents are administered by intravenous injection immediately prior to subjecting the patient to a magnetic resonance imaging procedure. The paramagnetic gadolinium ion alters the relaxation rates of the protons, enhancing the signal differentially in areas to which the gadolinium contrast agent has access. In patients with normal renal function, the agent (without the derivatized cyclodextrin) is eliminated through the kidneys with half lives in the order of several minutes to a few hours. As mentioned above, it is believed that the compositions described herein facilitate the agents' excretion through the kidney with a reduced toxic side effect and increased safety profile.

Thus, for example, various combinations of the invention can be administered parenterally including, inter alia, intravenous, intra-arterial, intramuscular, subcutaneous, and intraperitoneal and joint injection. Preferably, the formulation is for parenteral administration, for example, intravenous administration. Other routes of administration may be utilized as dictated by medical and pharmacological practice related to the desired use of the particular contrast agent employed.

It will be understood that the specific dose level for any particular patient will depend upon a variety of factors including the specific agent employed, the age, body weight, general health, sex, diet, time of administration, route of administration and rate of excretion.

Treatment of Water and Sequestration of Metal Ions

The uncomplexed ligand compounds described herein may be used to remove metal ion contaminants from water. Following chelation of such metal ions which may be radioactive or toxic, the metal ions may be recovered via subsequent processing which may include aggregation and filtration or chromatography.

Treatment of Diseases or Conditions Caused by Exposure to Metal Ions

The uncomplexed ligand compounds described herein may be used to treat individuals having a disease or condition caused by exposure to toxic and/or radioactive metal ions using the by the modes described hereinabove.

EQUIVALENTS AND SCOPE

Other than described herein, or unless otherwise expressly specified, all of the numerical ranges, amounts, values and percentages, such as those for amounts of materials, elemental contents, times and temperatures, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Any patent, publication, internet site, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Unless otherwise defined, all technical and scientific terms used herein have the same meaning as commonly understood by one of ordinary skill in the art to which this invention belongs.

While this invention has been particularly shown and described with references to embodiments thereof, it will be understood by those skilled in the art that various changes in form and details may be made therein without departing from the scope of the invention encompassed by the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context.

It is also noted that the term "comprising" is intended to be open and permits but does not require the inclusion of additional elements or steps. When the term "comprising" is used herein, the term "consisting of" is thus also encompassed and disclosed. Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where the term "about" is used, it is understood to reflect +/−10% of the recited value. In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein.

REFERENCES (1) Caravan, P.; Ellison, J. J.; McMurry, T. J.; Lauffer, R. B. Gadolinium(III) Chelates as MRI Contrast Agents: Structure, Dynamics, and Applications. Chem. Rev. 1999, 99 (9), 2293-2352 DOI: 10.1021/cr980440x.

(2) Hermann, P.; Kotek, J.; Kubíček, V.; Lukeš, I. Gadolinium(III) Complexes as MRI Contrast Agents: Ligand Design and Properties of the Complexes. Dalton Trans. 2008, 23, 3027-3047 DOI: 10. 1039/b719704g.

(3) Datta, A.; Raymond, K. N. Gd-Hydroxypyridinone (HOPO)-Based High-Relaxivity Magnetic Resonance Imaging (MRI) Contrast Agents. Acc. Chem. Res. 2009, 42 (7), 938-947 DOI: 10.1021/ar800250h.

(4) Rashid, H. U.; Martines, M. A. U.; Jorge, J.; de Moraes, P. M.; Umar, M. N.; Khan, K.; Rehman, H. U. Cyclen-Based Gd 3+ Complexes as MRI Contrast Agents: Relaxivity Enhancement and Ligand Design. Bioorg. Med. Chem. 2016, 24 (22), 5663-5684 DOI: 10.1016/j.bmc.2016.09.069.

(5) Fraum, T. J.; Ludwig, D. R.; Bashir, M. R.; Fowler, K. J. Gadolinium-Based Contrast Agents: A Comprehensive Risk Assessment: Gadolinium Risk Assessment. J. Magn. Reson. Imaging 2017, 46 (2), 338-353 DOI: 10.1002/jmri.25625.

(6) Idée, J.-M.; Port, M.; Medina, C.; Lancelot, E.; Fayoux, E.; Ballet, S.; Corot, C. Possible Involvement of Gadolinium Chelates in the Pathophysiology of Nephrogenic Systemic Fibrosis: A Critical Review. Toxicology 2008, 248 (2-3), 77-88 DOI: 10.1016/j.tox.2008.03.012.

(7) Schlaudecker, J. D.; Bernheisel, C. R. Gadolinium-Associated Nephrogenic Systemic Fibrosis. Am. Fam. Physician 2009, 80 (7), 711-714.

(8) Thomsen, H. S. Generic Gadolinium-Based Contrast Agents: The Future? Acta Radiol. 2017, 58 (11), 1285-1287 DOI: 10.1177/0284185117719576.

(9) Kotková, Z.; Helm, L.; Kotek, J.; Hermann, P.; Lukeš, I. Gadolinium Complexes of Monophosphinic Acid DOTA Derivatives Conjugated to Cyclodextrin Scaffolds: Efficient MRI Contrast Agents for Higher Magnetic Fields. Dalton Trans. 2012, 41 (43), 13509-13519 DOI: 10.1039/c2dt30858d.

(10) Skinner, P. J.; Beeby, A.; Dickins, R. S.; Parker, D.; Aime, S.; Botta, M. Conjugates of Cyclodextrins with Charged and Neutral Macrocyclic Europium, Terbium and Gadolinium Complexes: Sensitised Luminescence and Relaxometric Investigations and an Example of Supramolecular Relaxivity Enhancement. J. Chem. Soc. Perkin Trans. 2 2000, 7, 1329-1338 DOI: 10.1039/b0022071.

(11) Barge, A.; Cravotto, G.; Robaldo, B.; Gianolio, E.; Aime, S. New CD Derivatives as Self-Assembling Contrast Agents for Magnetic Resonance Imaging (MRI). J. Incl. Phenom. Macrocycl. Chem. 2007, 57 (1-4), 489-495 DOI: 10.1007/s10847-006-9239-2.

(12) Kotková, Z.; Kotek, J.; Jirák, D.; Jendelová, P.; Herynek, V.; Berková, Z.; Hermann, P.; Lukeš, I. Cyclodextrin-Based Bimodal Fluorescence/MRI Contrast Agents: An Efficient Approach to Cellular Imaging. Chem.-Eur. J. 2010, 16 (33), 10094-10102 DOI: 10.1002/chem.200903519.

(13) Bryson, J. M.; Chu, W.-J.; Lee, J.-H.; Reineke, T. M. A β-Cyclodextrin "Click Cluster" Decorated with Seven Paramagnetic Chelates Containing Two Water Exchange Sites. Bioconjug. Chem. 2008, 19 (8), 1505-1509 DOI: 10.1021/bc800200q.

(14) Barge, A.; Caporaso, M.; Cravotto, G.; Martina, K.; Tosco, P.; Aime, S.; Carrera, C.; Gianolio, E.; Pariani, G.; Corpillo, D. Design and Synthesis of a γ 1 β 8-Cyclodextrin Oligomer: A New Platform with Potential Application as a Dendrimeric Multicarrier. Chem.-Eur. J. 2013, 19 (36), 12086-12092 DOI: 10.1002/chem.201301215.

(15) Aime, S.; Botta, M.; Fedeli, F.; Gianolio, E.; Terreno, E.; Anelli, P. High-Relaxivity Contrast Agents for Magnetic Resonance Imaging Based on Multisite Interactions between a β-Cyclodextrin Oligomer and Suitably Functionalized GdIII Chelates. Chem.-Eur. J. 2001, 7 (24), 5261-5269 DOI: 10.1002/1521-3765(20011217)7:24<5261:AID-CHEM5261>3.0.CO;2-D.

(16) Aime, S.; Gianolio, E.; Arena, F.; Barge, A.; Martina, K.; Heropoulos, G.; Cravotto, G. New Cyclodextrin Dimers and Trimers Capable of Forming Supramolecular Adducts with Shape-Specific Ligands. Org Biomol Chem 2009, 7 (2), 370-379 DOI: 10.1039/B812172A.

(17) Gianolio, E.; Napolitano, R.; Fedeli, F.; Arena, F.; Aime, S. Poly-β-Cyclodextrin Based Platform for PH Mapping via a Ratiometric 19F/1H MRI Method. Chem. Commun. 2009, 40, 6044-6046 DOI: 10.1039/b914540k.

(18) Liu, T.; Li, X.; Qian, Y.; Hu, X.; Liu, S. Multifunctional PH-Disintegrable Micellar Nanoparticles of Asymmetrically Functionalized β-Cyclodextrin-Based Star Copolymer Covalently Conjugated with Doxorubicin and DOTA-Gd Moieties. Biomaterials 2012, 33 (8), 2521-2531 DOI: 10.1016/j.biomaterials.2011.12.013.

(19) Fredy, J. W.; Scelle, J.; Ramniceanu, G.; Doan, B.-T.; Bonnet, C. S.; Tóth, É.; Ménand, M.; Sollogoub, M.; Vives, G.; Hasenknopf, B. Mechanostereoselective One-Pot Synthesis of Functionalized Head-to-Head Cyclodextrin [3]Rotaxanes and Their Application as Magnetic Resonance Imaging Contrast Agents. Org. Lett. 2017, 19 (5), 1136-1139 DOI: 10.1021/acs.orglett.7b00153.

(20) Fredy, J. W.; Scelle, J.; Guenet, A.; Morel, E.; Adam de Beaumais, S.; Ménand, M.; Marvaud, V.; Bonnet, C. S.; Tóth, E.; Sollogoub, M.; Vives, G.; Hasenknopf, B. Cyclodextrin Polyrotaxanes as a Highly Modular Platform for the Development of Imaging Agents. Chem.-Eur. J. 2014, 20 (35), 10915-10920 DOI: 10.1002/chem.201403635.

(21) Martinelli, J.; Thangavel, K.; Tei, L.; Botta, M. Dendrimeric β-Cyclodextrin/Gd III Chelate Supramolecular Host-Guest Adducts as High-Relaxivity MRI Probes. Chem.-Eur. J. 2014, 20 (35), 10944-10952 DOI: 10.1002/chem.201402418.

(22) Aime, S.; Gianolio, E.; Terreno, E.; Menegotto, I.; Bracco, C.; Milone, L.; Cravotto, G. b-Cyclodextrin Adducts of Gd(III) Chelates: Useful Models for Investigating the Structural and Dynamic Determinants of the Relaxivity of Gadolinium-Based Systems. Magn. Reson. Chem. 2003, 41 (10), 800-805 DOI: 10.1002/mrc.1265.

(23) Aime, S.; Botta, M.; Frullano, L.; Crich, S. G.; Giovenzana, G. B.; Pagliarin, R.; Palmisano, G.; Sisti, M. Contrast Agents for Magnetic Resonance Imaging: A Novel Route to Enhanced Relaxivities Based on the Interaction of a GdIII Chelate with Poly-β-Cyclodextrins. Chem.-Eur. J. 1999, 5 (4), 1253-1260 DOI: 10.1002/(SICI)1521-3765(19990401)5:4<1253:AID-CHEM1253>3.0.CO;2-I.

(24) Battistini, E.; Gianolio, E.; Gref, R.; Couvreur, P.; Fuzerova, S.; Othman, M.; Aime, S.; Badet, B.; Durand, P. High-Relaxivity Magnetic Resonance Imaging (MRI) Contrast Agent Based on Supramolecular Assembly between a Gadolinium Chelate, a Modified Dextran, and Poly-β-Cyclodextrin. Chem.-Eur. J. 2008, 14 (15), 4551-4561 DOI: 10.1002/chem.200701587.

(25) Aime, S.; Gianolio, E.; Uggeri, F.; Tagliapietra, S.; Barge, A.; Cravotto, G. New Paramagnetic Supramolecular Adducts for MRI Applications Based on Non-Covalent Interactions between Gd(III)-Complexes and β- or γ-Cyclodextrin Units Anchored to Chitosan. J. Inorg. Biochem. 2006, 100 (5), 931-938 DOI: 10.1016/j.jinorgbio.2005.12.003.

(26) Zhou, Z.; Mondjinou, Y.; Hyun, S.-H.; Kulkarni, A.; Lu, Z.-R.; Thompson, D. H. Gd3+-1,4,7,10-Tetraazacyclododecane-1,4,7-Triacetic-2-Hydroxypropyl-β-Cyclodextrin/Pluronic Polyrotaxane as a Long Circulating High Relaxivity MRI Contrast Agent. ACS Appl. Mater. Interfaces 2015, 7 (40), 22272-22276 DOI: 10.1021/acsami.5b05393.

(27) Martinelli, J.; Fekete, M.; Tei, L.; Botta, M. Cleavable β-Cyclodextrin Nanocapsules Incorporating GdIII-Chelates as Bioresponsive MRI Probes. Chem. Commun. 2011, 47 (11), 3144-3146 DOI: 10.1039/c0cc05428c.

(28) Maffeo, D.; Lampropoulou, M.; Fardis, M.; Lazarou, Y. G.; Mavridis, I. M.; Mavridou, D. A. I.; Urso, E.; Pratsinis, H.; Kletsas, D.; Yannakopoulou, K. Novel Polycarboxylated EDTA-Type Cyclodextrins as Ligands for Lanthanide Binding: Study of Their Luminescence, Relaxivity Properties of Gd(III) Complexes, and PM3 Theoretical Calculations. Org. Biomol. Chem. 2010, 8 (8), 1910-1921 DOI: 10.1039/b924980j.

(29) Bonnet, C. S.; Fries, P. H.; Gadelle, A.; Gambarelli, S.; Delangle, P. A Rigorous Framework to Interpret Water Relaxivity. The Case Study of a Gd(III) Complex with an α-Cyclodextrin Derivative. J. Am. Chem. Soc. 2008, 130 (31), 10401-10413 DOI: 10.1021/ja802347r.

(30) Idriss, H.; Estour, F.; Zgani, I.; Barbot, C.; Biscotti, A.; Petit, S.; Galaup, C.; Hubert-Roux, M.; Nicol, L.; Mulder, P.; Gouhier, G. Effect of the Second Coordination Sphere on New Contrast Agents Based on Cyclodextrin Scaffolds for MRI Signals. RSC Adv. 2013, 3 (14), 4531-4534 DOI: 10.1039/c3ra40314a.

(31) Zgani, I.; Idriss, H.; Barbot, C.; Djedaïni-Pilard, F.; Petit, S.; Hubert-Roux, M.; Estour, F.; Gouhier, G. Positive Variation of the MRI Signal via Intramolecular Inclusion Complexation of a C-2 Functionalized β-Cyclodextrin. Org Biomol Chem 2017, 15 (3), 564-569 DOI: 10.1039/C6OB02583H.

(32) Gouhier, G.; et al. Unpublished Results.

(33) Almant, M.; Moreau, V.; Kovensky, J.; Bouckaert, J.; Gouin, S. G. Clustering of *Escherichia Coli* Type-1 Fimbrial Adhesins by Using Multimeric Heptyl α-D-Mannoside Probes with a Carbohydrate Core. Chem.-Eur. J. 2011, 17 (36), 10029-10038 DOI: 10.1002/chem.201100515.

(34) Abboud, J.-L. M.; Foces-Foces, C.; Notario, R.; Trifonov, R. E.; Volovodenko, A. P.; Ostrovskii, V. A.; Alkorta, I.; Elguero, J. Basicity of N—H— and N-Methyl-1, 2, 3-Triazoles in the Gas Phase, in Solution, and in the Solid State—An Experimental and Theoretical Study. Eur. J. Org. Chem. 2001, 2001 (16), 3013-3024 DOI: 10.1002/1099-0690(200108)2001:16<3013:AID-EJOC3013>3.0.CO;2-Y.

(35) Long, X.-H.; Yang, P.-Y.; Liu, Q.; Yao, J.; Wang, Y.; He, G.-H.; Hong, G.-Y.; Ni, J.-Z. Metabolomic Profiles Delineate Potential Roles for Gadolinium Chloride in the Proliferation or Inhibition of Hela Cells. BioMetals 2011, 24 (4), 663-677 DOI: 10.1007/s10534-011-9419-4.

(36) Rudovskjỳ, J.; Botta, M.; Hermann, P.; Koridze, A.; Aime, S. Relaxometric and Solution NMR Structural Studies on Ditopic Lanthanide (III) Complexes of a Phosphinate Analogue of DOTA with a Fast Rate of Water Exchange. Dalton Trans. 2006, 19, 2323-2333 DOI: 10.1039/B518147J.

(37) Fatin-Rouge, N.; Bünzli, J.-C. G. Thermodynamic and Structural Study of Inclusion Complexes between Trivalent Lanthanide Ions and Native Cyclodextrins. Inorganica Chim. Acta 1999, 293 (1), 53-60 DOI: 10.1016/S0020-1693(99)00227-3.

(38) Cacheris, W. P.; Quay, S. C.; Rocklage, S. M, The relationship between thermodynamics and the toxicity of gadolinium complexes. Magn. Reson. Imaging, 1990, 8, 467-481

(39) Burgess, J.; Rangel, M. Hydroxypyranones, Hydroxypyridinones, and Their Complexes. In Advances in Inorganic Chemistry; van Eldik, R., Ed.; Academic Press, 2008; Vol. 60, pp 167-243.

(40) Supkowski, R. M.; Horrocks, W. D. On the Determination of the Number of Water Molecules, q, Coordinated to Europium(III) Ions in Solution from Luminescence Decay Lifetimes. Inorganica Chim. Acta 2002, 340 (Supplement C), 44-48 DOI: 10.1016/S0020-1693(O2) 01022-8.

(41) Harborg et al. Assay of the active ingredient of an MRI contrast agent using mid and near infrared spectroscopy and multivariate calibration. J. Molecul. Structure 1995, 348: 139-142.

(42) Tweedle et al. Biodistribution of Radiolabeled, Formulated Gadopentetate, Gadoteridol, Gadoterate, and Gadodiamide in Mice and Rats. Invest. Radiol. 1995, 30(6): 372-380).

Each reference in this list is incorporated herein by reference in its entirety.

The invention claimed is:

1. A compound of formula $M_z(L)$, wherein:
M is a metal ion;
L is a ligand of formula I A-[W—X—Y—N(CH$_2$COOH)$_2$]$_n$     (formula I);

and
z is an integer of 1 to 4,
wherein, with reference to formula I,
A is cyclodextrin or a derivative thereof, a disaccharide, starch or other carbohydrate polymer;
W is a chemical bond, or a linker comprising a substituted or unsubstituted $C_1$-$C_5$ carbon chain;
X is a five or six membered ring having one or more heteroatoms;
Y is a linker comprising a substituted or unsubstituted $C_1$-$C_3$ carbon chain; and
n is an integer of 2 to 8.

2. The compound of claim 1, wherein the five membered ring is 1,2,3-triazole.

3. The compound of claim 1, wherein A is a cyclodextrin derivative with one of three hydroxyl groups of one or more glucopyranosyl units substituted with a linking atom selected from the group consisting of: N, S and O.

4. The compound of claim 1, wherein A is a cyclodextrin derivative with one or more glucopyranosyl units having one or more free hydroxyl groups replaced with a $C_1$-$C_{18}$ alkoxy group or a $C_1$-$C_{18}$ acyl group.

5. The compound of claim 1, wherein the cyclodextrin or the cyclodextrin derivative is an alpha-cyclodextrin and n is an integer of 2 to 6, a beta-cyclodextrin and n is an integer of 2 to 7, or a gamma-cyclodextrin and n is an integer of 2 to 8.

6. The compound of claim 1, wherein the metal ion is a lanthanide ion or an actinide ion having a charge in a range of +1 to +7.

7. The compound of claim 6, wherein the metal ion is a lanthanide ion and the lanthanide ion is selected from Gd(III), Yb(III) or Eu(III).

8. The compound of claim 7, wherein the metal ion is coordinated by functional groups contained in two adjacent W—X—Y—N(CH$_2$COO$^-$)$_2$ moieties of the formula A-[W—X—Y—N(CH$_2$COOH)$_2$]$_n$.

9. The compound of claim 8, wherein the W—X—Y—N(CH$_2$COOH)$_2$ moiety is linked to the cyclodextrin at position C6 of one or more of the glucopyranosyl units of the cyclodextrin.

10. The compound of claim 8, wherein the metal ion has an octahedral coordination, and the octahedral coordination is:

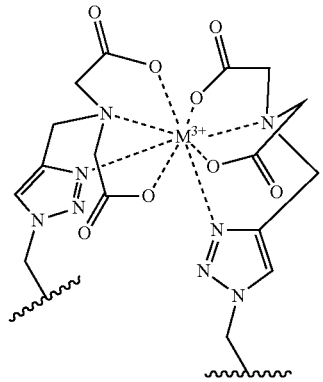

wherein the dashed lines indicate coordination bonds between the two adjacent W—X—Y—N(CH$_2$COO$^-$)$_2$ moieties of formula I of A-[W—X—Y—N(CH$_2$COOH)$_2$]$_n$ and the metal ion.

11. The compound of claim 1, wherein, in formula I, A-[W—X—Y—N(CH$_2$COOH)$_2$]$_n$, the [W—X—Y—N(CH$_2$COOH)$_2$] moiety is in a deprotonated form of:

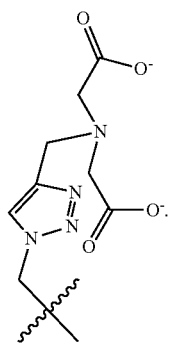

12. The compound of claim 1, wherein the W—X—Y—N(CH$_2$COOH)$_2$ moiety is linked to an amphiphilic cyclodextrin which has hydrophobic chains on its secondary face.

13. The compound of claim 1, wherein A is a disaccharide and n is 2.

14. The compound of claim 13, wherein the disaccharide is maltose, sucrose, lactose, lactosamine, cellulobiose or trehalose.

15. A contrast agent comprising the compound of claim 1 and a pharmaceutically acceptable carrier or diluent.

16. A method of acquiring an image, the method comprising:
   a) administering the contrast agent of claim 15 to a tissue, cell or patient; and
   b) acquiring a magnetic resonance image of the cell, tissue or patient.

17. A method for treatment of water by removal of metal ions from the water, the method comprising contacting the water with the compound of claim 1.

18. A method for treatment of water by removal of organic contaminants, the method comprising contacting the water with the compound of claim 1.

19. A method for treatment of a disease or condition caused by the presence of heavy metal ions or radioactive metal ions, the method comprising administering a composition comprising the compound of claim 1 to a patient.

20. A method for recovery of radioactive metal ions or precious metal ions from waste water, the method comprising:
   contacting the waste water with the compound of claim 1 to form aggregates of the radioactive metal ions or precious metal ions; and
   recovering the aggregates by filtration or chromatography.

\* \* \* \* \*